(12) United States Patent
Hakansson et al.

(10) Patent No.: US 11,324,867 B2
(45) Date of Patent: May 10, 2022

(54) BLOOD CIRCUIT PRESSURE GRAPHICAL ELEMENT FOR MEDICAL TREATMENT USER INTERFACES

(71) Applicant: GAMBRO LUNDIA AB, Lund (SE)

(72) Inventors: Annmargret Hakansson, Kagerod (SE); Bendik Torvin, Schaanwald (LI); Roger Nilsson, Hoor (SE); Per Ogren, Malmo (SE)

(73) Assignee: Gambro Lundia AB, Lund (SE)

( * ) Notice: Subject to any disclaimer, the term of this patent is extended or adjusted under 35 U.S.C. 154(b) by 607 days.

(21) Appl. No.: 16/090,432

(22) PCT Filed: Mar. 30, 2017

(86) PCT No.: PCT/EP2017/057486
§ 371 (c)(1),
(2) Date: Oct. 1, 2018

(87) PCT Pub. No.: WO2017/167845
PCT Pub. Date: Oct. 5, 2017

(65) Prior Publication Data
US 2019/0111199 A1 Apr. 18, 2019

(30) Foreign Application Priority Data
Apr. 1, 2016 (SE) .................................. 1650433-4

(51) Int. Cl.
*A61M 1/14* (2006.01)
*A61M 1/34* (2006.01)
(Continued)

(52) U.S. Cl.
CPC ............... *A61M 1/14* (2013.01); *A61M 1/34* (2013.01); *A61M 1/36* (2013.01); *G16H 20/40* (2018.01);
(Continued)

(58) Field of Classification Search
None
See application file for complete search history.

(56) References Cited

U.S. PATENT DOCUMENTS

| 4,845,723 A | 7/1989 | Heinen |
| 7,297,129 B2 | 11/2007 | Kinouchi |

(Continued)

FOREIGN PATENT DOCUMENTS

| DE | 19742633 | 4/1999 |
| EP | 2719404 | 4/2014 |

(Continued)

OTHER PUBLICATIONS

PCT Search Report and Written Opinion for PCT/EP2017/057486 dated Jun. 29, 2017 (15 pages).

*Primary Examiner* — Hayden Brewster
(74) *Attorney, Agent, or Firm* — Mueting Raasch Group

(57) ABSTRACT

Graphical user interfaces for use with extracorporeal blood treatment systems may include a blood circuit pressure graphical element. The blood circuit pressure graphical element may include a venous portion and an arterial portion. The venous portion may depict, or include, a presently-monitored venous blood circuit pressure value and a graphical representation of previously-monitored venous blood circuit pressure values, and the arterial portion may depict, or include, a presently-monitored arterial blood circuit pressure value and a graphical representation of previously-monitored arterial blood circuit pressure values.

38 Claims, 17 Drawing Sheets

(51) Int. Cl.
*A61M 1/36* (2006.01)
*G16H 40/63* (2018.01)
*G16H 20/40* (2018.01)
*G16H 50/30* (2018.01)
*G16H 50/20* (2018.01)

(52) U.S. Cl.
CPC ............ *G16H 40/63* (2018.01); *G16H 50/20* (2018.01); *G16H 50/30* (2018.01); *A61M 2205/3331* (2013.01); *A61M 2205/3334* (2013.01); *A61M 2205/502* (2013.01)

(56) References Cited

U.S. PATENT DOCUMENTS

| | | |
|---|---|---|
| 7,318,892 B2 | 1/2008 | Connell |
| 7,988,850 B2 | 8/2011 | Roncadi |
| 8,871,095 B2 | 10/2014 | Yu |
| 2004/0184953 A1 | 9/2004 | Litzie |
| 2005/0045540 A1 | 3/2005 | Connell |
| 2008/0077072 A1 | 3/2008 | Keenan |
| 2008/0249377 A1 | 10/2008 | Molducci |
| 2008/0307353 A1 | 10/2008 | Molducci |
| 2012/0138533 A1 | 6/2012 | Curtis |
| 2013/0201222 A1 | 8/2013 | Doyle |
| 2013/0298062 A1 | 11/2013 | Dolgos |
| 2013/0331775 A1 | 12/2013 | Britton |
| 2014/0102959 A1* | 4/2014 | Furuhashi ............... A61M 1/14 210/85 |
| 2016/0038665 A1* | 2/2016 | Schaefer ................ A61M 1/14 137/551 |
| 2017/0147166 A1* | 5/2017 | Schaefer ................ A61M 1/14 |

FOREIGN PATENT DOCUMENTS

| | | | |
|---|---|---|---|
| WO | WO 94/11093 | 5/1994 | |
| WO | WO 2014/151669 | 9/2014 | |
| WO | WO 2015/153253 | 10/2015 | |
| WO | WO 2015/153254 | 10/2015 | |
| WO | WO-2015153253 A1 * | 10/2015 | ........... G06F 3/0482 |

* cited by examiner

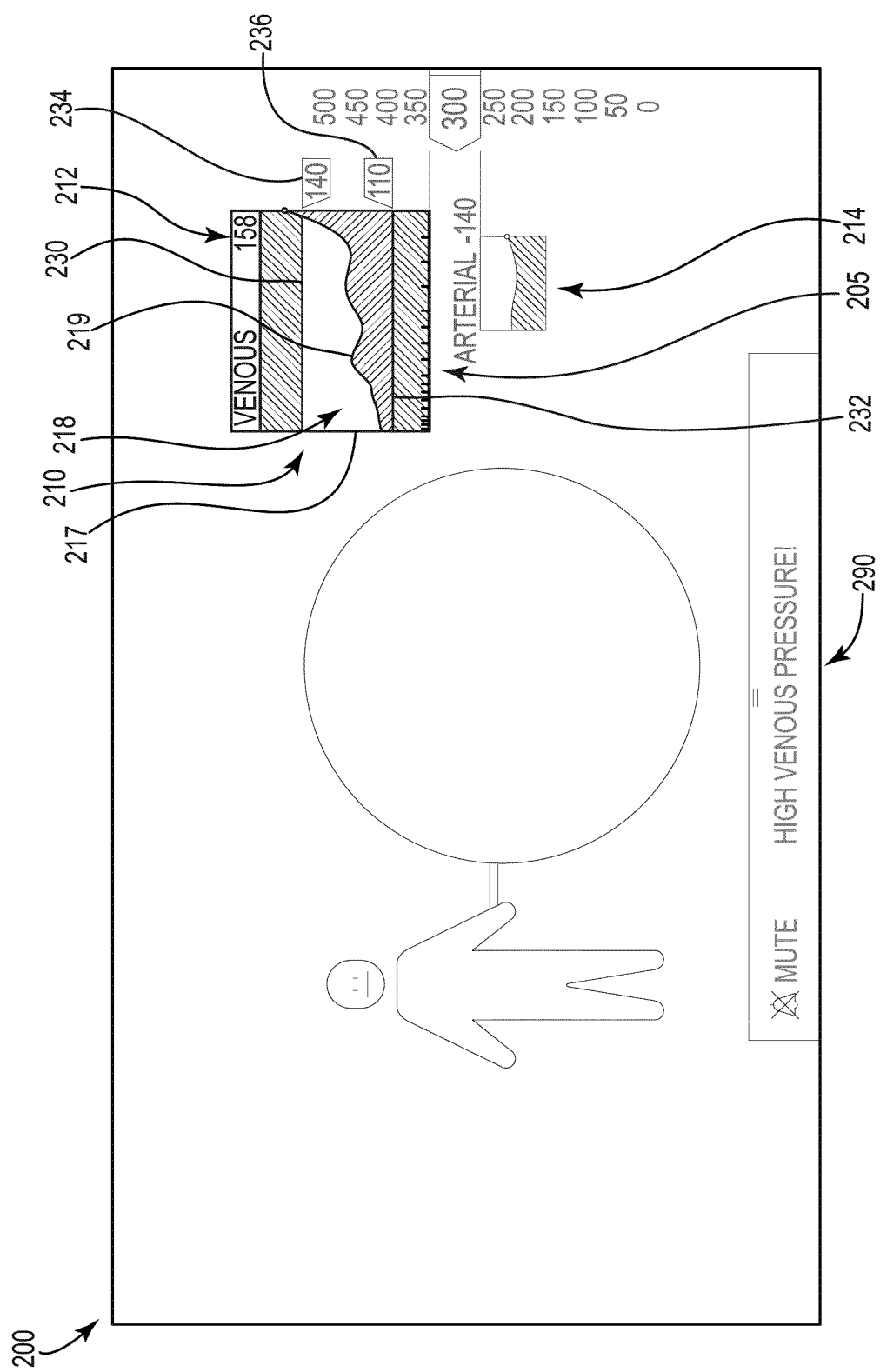

BLOOD CIRCUIT PRESSURE GRAPHICAL ELEMENT FOR MEDICAL TREATMENT USER INTERFACES

This application is a U.S. National Stage Application of International Application No. PCT/EP2017/057486, filed 2017 Mar. 30 and published in English on 2017 Oct. 5 as International Publication No. WO 2017/167845 A1, which claims the benefit of priority under 35 U.S.C. § 119(a) of Swedish Patent Application No. 1650433-4 filed 2016 Apr. 1, each of which are incorporated herein by reference in their entireties.

The disclosure herein relates to medical treatment apparatus. More particularly, the disclosure relates to systems and methods for use in providing graphical user interfaces related to medical treatment apparatus such as extracorporeal blood treatment apparatus.

Medical treatment apparatus often includes a graphical user interface depicted on a display. A user may use the graphical user interface to, among other things, configure and setup a treatment, monitor and perform a treatment, and perform various post-treatment processes. The graphical user interface for treatment apparatus may include a plurality of different graphical elements, graphical regions, and graphical areas configured for performing the functionality associated with the treatment apparatus.

Medical treatment apparatus may be configured to perform extracorporeal blood treatment. Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating such undesirable matter from their blood, for example, in the case of a patient who is suffering from temporary or permanent kidney failure. These and other patients may, for instance, undergo extracorporeal blood treatment to add to or to eliminate matter from their blood, to maintain an acid-base balance, and/or to eliminate excess body fluids.

SUMMARY

The present disclosure describes systems and methods that use, or utilize, graphical user interfaces that depict one or more graphical elements that may be used to view information related to a medical treatment performed by a medical system and to adjust one or more parameters or values associated with the medical treatment. Such one or more parameters may include venous and arterial blood circuit pressures and upper and/or lower alarm limits associated with each of the venous and arterial blood circuit pressures. Graphical user interfaces may not provide enough information with respect to each of the venous and arterial blood circuit pressures such that a user may ascertain, or recognize, current or historical information related venous and arterial blood circuit pressures. Such graphical user interfaces may require users to perform cumbersome and time-consuming processes, or steps, to be presented with additional information with respect to blood circuit pressures such as previously-monitored values related to venous and arterial blood circuit pressures. Further, graphical user interfaces may not position and/or animate the graphics depicting the venous and arterial blood circuit pressures to draw the attention of a user, e.g., when an alarm limit is reached or nearly reached, when an alarm is triggered. Still further, graphical user interfaces may not allow a user to view historical, or previously-monitored, venous and arterial blood circuit pressures. Yet still further, monitoring blood circuit pressure may be important when adjusting blood flow rate, and previous graphical user interfaces have located blood circuit pressure information apart and away from (e.g. on different locations on the graphical user interface) where the blood flow rate is adjusted. A user's attention may be directed at the blood flow rate adjustment and not directed at the blood circuit pressure information when adjusting blood flow rate. Thus, a user may need to disengage from adjusting blood flow rate to determine blood circuit pressure rate status, then re-engage with the blood flow rate adjustment in response thereto, and so on until the proper blood flow rate is set without negatively affecting the blood circuit pressures, which may be a tedious and cumbersome process.

The exemplary graphical user interfaces may include a blood circuit pressure graphical element configured to depict information with respect a venous blood circuit and an arterial blood circuit used in an extracorporeal blood treatment system to perform an extracorporeal blood treatment. The blood circuit pressure graphical element may include present venous and arterial blood circuit pressures of the extracorporeal blood treatment and graphical representations of past venous and arterial blood circuit pressures of the extracorporeal blood treatment. The graphical representations of previously-monitored venous and arterial blood circuit pressure values of the extracorporeal blood treatment may overcome the problems of previous graphical user interfaces that did not provide enough information with respect to each of the venous and arterial blood circuit pressures. For example, the blood circuit pressure graphical elements described herein may allow users to quickly and efficiently ascertain, or recognize, current and previously-monitored values related to venous and arterial blood circuit pressure. In other words, blood circuit pressure graphical elements described herein may allow users to ascertain current and previous blood circuit pressure values "at a glance" without performing additional cumbersome and time-consuming processes to acquire such information. The blood circuit pressure graphical element and/or one or more portions or regions thereof may be selectable and/or movable by a user to change venous and arterial blood circuit pressure alarm limits of the extracorporeal blood treatment and view additional information such as additional past venous and arterial blood circuit pressure data of the extracorporeal blood treatment.

The blood circuit pressure graphical element, and elements thereof, may be described as a "controller" with respect to the various parameters associated with the blood circuit pressures of an extracorporeal blood treatment that may be used to control, or adjust, such associated parameters. Further, each element of the blood circuit pressure graphical element such as, e.g., venous and arterial portions, may be described as providing control of events or conditions (e.g., parameters, limits, etc.) that are internal to the technical medical treatment system or apparatus. Still further, each element of the blood circuit pressure graphical element such as, e.g., venous and arterial portions, may be described as a way, or process, by which the medical treatment system, or apparatus, prompts a user to interact with the system, or apparatus, so as to in a way to enable proper functionality of the system to perform one or more medical treatment such as, e.g., extracorporeal blood treatments. For example, the blood circuit pressure graphical element may be used to adjust one or more limits associated with each of the venous and arterial blood circuit pressures of an on-going extracorporeal blood treatment. Yet still further, each of the parameters related to the medical treatment that are associated with the blood circuit graphical element may be described as presenting cognitive information constituting, or representing, one or more states such as, e.g., operational states, alarm, states, and warning states, of the medical system. And still further, the blood circuit pressure graphical element may be described as providing technical information intrinsically tied to, or associated with, the medical system and the medical treatments performable by the medical system and as providing control, or adjustment of the technical information to control, or adjust, actual functional characteristics (e.g., blood circuit pressure alarm limits) of the medical system and/or medical treatments performable thereby. For example, the exemplary blood circuit pressure graphical element described herein may be graphically emphasized in response to adjustment of blood flow rate using a blood flow rate adjustment graphical element such that a user may easily ascertain the blood circuit pressure information while adjustment of the blood flow rate is performed. The graphical emphasis of the blood circuit pressure graphical element may include movement of the blood circuit pressure graphical element with a blood flow rate adjustment graphical element such that a user's attention will already be directed at a location proximate the blood circuit pressure graphical element during adjustment of blood flow rate with the blood flow rate adjustment graphical element. Such graphical emphasis of the blood circuit graphical element may avoid the tedious and cumbersome process of engagement and disengagement of blood flow rate adjustment required by previous graphical user interfaces.

One exemplary extracorporeal blood treatment system may include extracorporeal blood treatment apparatus including one or more pumps, a venous blood circuit, an arterial blood circuit, and one or more blood circuit pressure sensors to measure venous blood circuit pressure in the venous blood circuit and arterial blood circuit pressure in the arterial blood circuit. The exemplary extracorporeal blood treatment system may further include a display including a graphical user interface configured to depict a blood circuit pressure graphical element corresponding to the measured venous blood circuit pressure and arterial blood circuit pressure and a blood flow rate area corresponding to blood flow rate of the extracorporeal blood treatment performable using the extracorporeal blood treatment apparatus. The exemplary system may further include a processor operatively coupled to the display and the extracorporeal blood treatment apparatus and configured to display the blood flow rate area on the graphical user interface depicting a present blood flow rate value of the extracorporeal blood treatment and including a blood flow rate adjustment graphical element and allow a user to move the blood flow rate adjustment graphical element to adjust the blood flow rate of the extracorporeal blood treatment using the one or more pumps of the extracorporeal blood treatment apparatus. The processor may be further configured to monitor venous blood circuit pressure in the venous blood circuit and arterial blood circuit pressure in the arterial blood circuit of the extracorporeal blood treatment using the one or more blood circuit pressure sensors of the extracorporeal blood treatment apparatus and display the blood circuit pressure graphical element (e.g., in proximity to the blood flow rate adjustment graphical element) on the graphical user interface. The blood circuit pressure graphical element may be graphically emphasized in response to the blood flow rate adjustment graphical element being moved to adjust the blood flow rate of the extracorporeal blood treatment using the one or more pumps of the extracorporeal blood treatment apparatus. Further, the blood circuit pressure graphical element may include a venous portion and an arterial portion. The venous portion may include a presently-monitored venous blood circuit pressure value of the extracorporeal blood treatment and a graphical representation of previously-monitored venous blood circuit pressure values of the extracorporeal blood treatment, and the arterial portion may include a presently-monitored arterial blood circuit pressure value of the extracorporeal blood treatment and a graphical representation of previously-monitored arterial blood circuit pressure values of the extracorporeal blood treatment.

One exemplary method for an extracorporeal blood treatment system may include providing extracorporeal blood treatment apparatus including one or more pumps, a venous blood circuit, an arterial blood circuit, and one or more blood circuit pressure sensors to measure venous blood circuit pressure in the venous blood circuit and arterial blood circuit pressure in the arterial blood circuit. The exemplary method may further include displaying a blood flow rate area on a graphical user interface depicting a present blood flow rate value of the extracorporeal blood treatment and including a blood flow rate adjustment graphical element and allowing a user to move the blood flow rate adjustment graphical element to adjust the blood flow rate of the extracorporeal blood treatment using the one or more pumps of the extracorporeal blood treatment apparatus. The exemplary method may further include monitoring venous blood circuit pressure in the venous blood circuit of the extracorporeal blood treatment apparatus using the one or more blood circuit pressure sensors and arterial blood circuit pressure in the arterial blood circuit of the extracorporeal blood treatment apparatus using the one or more blood circuit pressure sensors and displaying a blood circuit pressure graphical element on the graphical user interface (e.g., in proximity to the blood flow rate adjustment graphical element). The blood circuit pressure graphical element may be graphically emphasized in response to the blood flow rate of the extracorporeal blood treatment being adjusted using the blood flow rate adjustment graphical element. Further, the blood circuit pressure graphical element may include a venous portion and an arterial portion. The venous portion may include a presently-monitored venous blood circuit pressure value of the extracorporeal blood treatment and a graphical representation of previously-monitored venous blood circuit pressure values of the extracorporeal blood treatment. The arterial portion may include a presently-monitored arterial blood circuit pressure value of the extracorporeal blood treatment and a graphical representation of previously-monitored arterial blood circuit pressure values of the extracorporeal blood treatment.

In one or more embodiments, the blood circuit pressure graphical element may move with the blood flow rate adjustment graphical element in response to the blood flow rate being adjusted using the blood flow rate adjustment graphical element. In other words, the graphical emphasis of the blood circuit pressure graphical element in response to the blood flow rate being adjusted using the blood flow rate adjustment graphical element may be the movement of the blood circuit pressure graphical element with the blood flow rate adjustment graphical element.

In one or more embodiments, a graphical size of at least a portion of the blood circuit pressure graphical element may be expanded in response to the blood flow rate being adjusted using the blood flow rate adjustment graphical element.

One exemplary extracorporeal blood treatment system may include extracorporeal blood treatment apparatus including one or more pumps, a venous blood circuit, an arterial blood circuit, and one or more blood circuit pressure sensors to measure venous blood circuit pressure in the venous blood circuit and arterial blood circuit pressure in the arterial blood circuit. The exemplary extracorporeal blood treatment system may further include a display including a graphical user interface configured to depict a blood circuit pressure graphical element corresponding to the measured venous blood circuit pressure and arterial blood circuit pressure, a blood treatment graphical element corresponding to one or more blood treatment processes of the extracorporeal blood treatment performable using the extracorporeal blood treatment apparatus, and a patient graphical element symbolically depicting a patient undergoing the extracorporeal blood treatment using the extracorporeal blood treatment apparatus. The exemplary system may further include a processor operatively coupled to the display and the extracorporeal blood treatment apparatus. The processor may be configured to monitor venous blood circuit pressure in the venous blood circuit and arterial blood circuit pressure in the arterial blood circuit using the one or more blood circuit pressure sensors of the extracorporeal blood treatment apparatus, display the blood treatment graphical element and the patient graphical element on the graphical user interface, and display the blood circuit pressure graphical element between the blood treatment graphical element and the patient graphical element on the graphical user interface to indicate that the venous and arterial blood circuit pressures monitored from the venous and arterial blood circuits of the extracorporeal blood treatment apparatus. The blood circuit pressure graphical element may include a venous portion and an arterial portion. The venous portion may include a presently-monitored venous blood circuit pressure value of the extracorporeal blood treatment and a graphical representation of previously-monitored venous blood circuit pressure values of the extracorporeal blood treatment. The arterial portion may include a presently-monitored arterial blood circuit pressure value of the extracorporeal blood treatment and a graphical representation of previously-monitored arterial blood circuit pressure values of the extracorporeal blood treatment.

One exemplary method for an extracorporeal blood treatment system may include providing extracorporeal blood treatment apparatus including one or more pumps, a venous blood circuit, an arterial blood circuit, and one or more blood circuit pressure sensors to measure venous blood circuit pressure in the venous blood circuit and arterial blood circuit pressure in the arterial blood circuit. The exemplary method may further include displaying a blood treatment graphical element corresponding to one or more processes of the extracorporeal blood treatment performable using the extracorporeal blood treatment apparatus and a patient graphical element symbolically depicting a patient undergoing the extracorporeal blood treatment using extracorporeal blood treatment apparatus on a graphical user interface and monitoring venous blood circuit pressure in the venous blood circuit of the extracorporeal blood treatment and arterial blood circuit pressure in the arterial blood circuit of the extracorporeal blood treatment using the one or more blood circuit pressure sensors of the extracorporeal blood treatment apparatus. The exemplary method may further include displaying the blood circuit pressure graphical element between the blood treatment graphical element and the patient graphical element on a graphical user interface to indicate that the venous and arterial blood circuit pressures are monitored from the venous and arterial blood circuits of the extracorporeal blood treatment apparatus. The blood circuit pressure graphical element may include a venous portion and an arterial portion. The venous portion may include a presently-monitored venous blood circuit pressure value of the extracorporeal blood treatment and a graphical representation of previously-monitored venous blood circuit pressure values of the extracorporeal blood treatment. The arterial portion may include a presently-monitored arterial blood circuit pressure value of the extracorporeal blood treatment and a graphical representation of previously-monitored arterial blood circuit pressure values of the extracorporeal blood treatment.

In one or more embodiments, the presently-monitored venous blood circuit pressure value may include at least one of an alphanumeric representation of the presently-monitored venous blood circuit pressure value and a graphical representation of the presently-monitored venous blood circuit pressure value proximate the graphical representation of previously-monitored venous blood circuit pressure values, and the presently-monitored arterial blood circuit pressure value may include at least one of an alphanumeric representation of the presently-monitored arterial blood circuit pressure value and a graphical representation of the presently-monitored arterial blood circuit pressure value proximate the graphical representation of previously-monitored arterial blood circuit pressure values.

In one or more embodiments, the venous portion of the blood circuit pressure graphical element may further include a venous circuit pressure alarm limit graphical representation indicative of a venous circuit pressure alarm limit value for the monitored venous blood circuit pressure, and the venous circuit pressure alarm limit graphical representation may be located in relation to the presently-monitored venous blood circuit pressure value to graphically indicate a quantitative difference between the presently-monitored venous blood circuit pressure value and the venous circuit pressure alarm limit value. Further, the arterial portion of the blood circuit pressure graphical element may further include an arterial circuit pressure alarm limit graphical representation indicative of a arterial circuit pressure alarm limit value for the monitored arterial blood circuit pressure, and the arterial circuit pressure alarm limit graphical representation may be located in relation to the presently-monitored arterial blood circuit pressure value to graphically indicate a quantitative difference between the presently-monitored arterial blood circuit pressure value and the arterial circuit pressure alarm limit value. Further, the processor may be further configured to execute or the methods may further include allowing a user to select the venous circuit pressure alarm limit graphical representation to adjust the venous circuit pressure alarm limit value, and allowing a user to select the arterial circuit pressure alarm limit graphical representation to adjust the arterial circuit pressure alarm limit value. In at least one embodiment, the processor may be further configured to execute or the methods may further include allowing a user to select and drag the venous circuit pressure alarm limit graphical representation upwardly to increase the venous circuit pressure alarm limit value and downwardly to decrease the venous circuit pressure alarm limit value, and allowing a user to select and drag the arterial circuit pressure alarm limit graphical representation upwardly to increase the arterial circuit pressure alarm limit value and downwardly to decrease the arterial circuit pressure alarm limit value. In at least one embodiment the venous circuit pressure alarm limit graphical representation may only displayed in response to the presently-monitored venous blood circuit pressure value being within a selected value of the venous circuit pressure alarm limit value and the arterial circuit pressure alarm limit graphical representation may only displayed in response to the presently-monitored arterial blood circuit pressure value being within a selected value of the arterial circuit pressure alarm limit value.

In one or more embodiments, the venous portion of the blood circuit pressure graphical element may further include an upper venous circuit pressure alarm limit graphical representation indicative of an upper venous circuit pressure alarm limit value for the monitored venous blood circuit pressure and a lower venous circuit pressure alarm limit graphical representation indicative of a lower venous circuit pressure alarm limit value for the monitored venous blood circuit pressure. Further, the upper and lower venous circuit pressure alarm limit graphical representations may be located in relation to the presently-monitored venous blood circuit pressure value to graphically indicate quantitative differences between the presently-monitored venous blood circuit pressure value and the upper and lower venous circuit pressure alarm limit values. Still further, the processor may be further configured to execute or the method may further include allowing a user to select and drag the venous portion upwardly to simultaneously increase both of the upper and lower venous circuit pressure alarm limit values and downwardly to simultaneously decrease both of the upper and lower venous circuit pressure alarm limit values.

In one or more embodiments, the arterial portion of the blood circuit pressure graphical element may further include an upper arterial circuit pressure alarm limit graphical representation indicative of an upper arterial circuit pressure alarm limit value for the monitored arterial blood circuit pressure and a lower arterial circuit pressure alarm limit graphical representation indicative of a lower arterial circuit pressure alarm limit value for the monitored arterial blood circuit pressure. Further, the upper and lower arterial circuit pressure alarm limit graphical representations may be located in relation to the presently-monitored arterial blood circuit pressure value to graphically indicate quantitative differences between the presently-monitored arterial blood circuit pressure value and the upper and lower arterial circuit pressure alarm limit values. Still further, the processor may be further configured to execute or the method may further include allowing a user to select and drag the arterial portion upwardly to simultaneously increase both of the upper and lower arterial circuit pressure alarm limit values and downwardly to simultaneously decrease both of the upper and lower arterial circuit pressure alarm limit values. In at least one embodiment, the processor may be further configured to execute or the method may further include allowing a user to automatically reset both of the upper and lower venous circuit pressure alarm limit values centered around the presently-monitored venous blood circuit pressure value and allowing a user to automatically reset both of the upper and lower arterial circuit pressure alarm limit values centered around the presently-monitored arterial blood circuit pressure value.

In one or more embodiments, the graphical representation of previously-monitored venous blood circuit pressure values may include a venous blood circuit pressure line graph plotting the previously-monitored venous blood circuit pressure values over a trailing time period prior to the present and the graphical representation of previously-monitored arterial blood circuit pressure values may include an arterial blood circuit pressure line graph plotting the previously-monitored arterial blood circuit pressure values over the trailing time period prior to the present. In at least one embodiment, the trailing time period may be a linear time period. In at least one embodiment, the trailing time period may be a non-linear time period. In at least one embodiment, the venous portion of the blood circuit pressure graphical element may be selectable by a user to expand a graphical size of the venous portion on the graphical user interface increasing the displayable trailing time period of the venous blood circuit pressure line graph, and the arterial portion of the blood circuit pressure graphical element may be selectable by a user to expand a graphical size of the arterial portion on the graphical user interface increasing the displayable trailing time period of the arterial blood circuit pressure line graph. Further, expanding the graphical size of the venous portion further may increase the displayable range of venous blood circuit pressure values of the venous blood circuit pressure line graph, and expanding the graphical size of the arterial portion further may increase the displayable range of arterial blood circuit pressure values of the arterial blood circuit pressure line graph.

In one or more embodiments, the graphical user interface may be configured to depict a graphical representation of one or more blood lines extending from the patient graphical element to the blood treatment graphical element to indicate that the patient is connected to the extracorporeal blood treatment system for the extracorporeal blood treatment, and the blood circuit pressure graphical element may be located along the graphical representation of the one or more blood lines. In one or more embodiments, the blood circuit pressure graphical element may only be displayed on the graphical user interface in response to the patient being connected to at least one of the venous and arterial blood circuits of the extracorporeal blood treatment system.

In one or more embodiments, at least one of the venous portion and the arterial portion of the blood circuit pressure graphical element may be graphically emphasized in response to issuance of a blood circuit pressure alarm state. In at least one embodiment, a graphical size of at least one of the venous portion and the arterial portion of the blood circuit pressure graphical element on the graphical user interface may be increased in response to issuance of the blood circuit pressure alarm state.

In one or more embodiments, the graphical user interface other than the at least one of the venous portion and the arterial portion of the blood circuit pressure graphical element that is graphically emphasized may be graphically de-emphasized in response to issuance of the blood circuit pressure alarm state.

In one or more embodiments, the display may include a touchscreen.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

BRIEF DESCRIPTION OF THE DRAWING

FIGS. 3A-3F depict an exemplary graphical user interface for use in monitoring and/or adjusting blood circuit pressure information during a blood treatment using an extracorporeal blood treatment system such as, for example, shown generally in FIGS. 1-2.

DETAILED DESCRIPTION OF EXEMPLARY EMBODIMENTS

Figure 1:
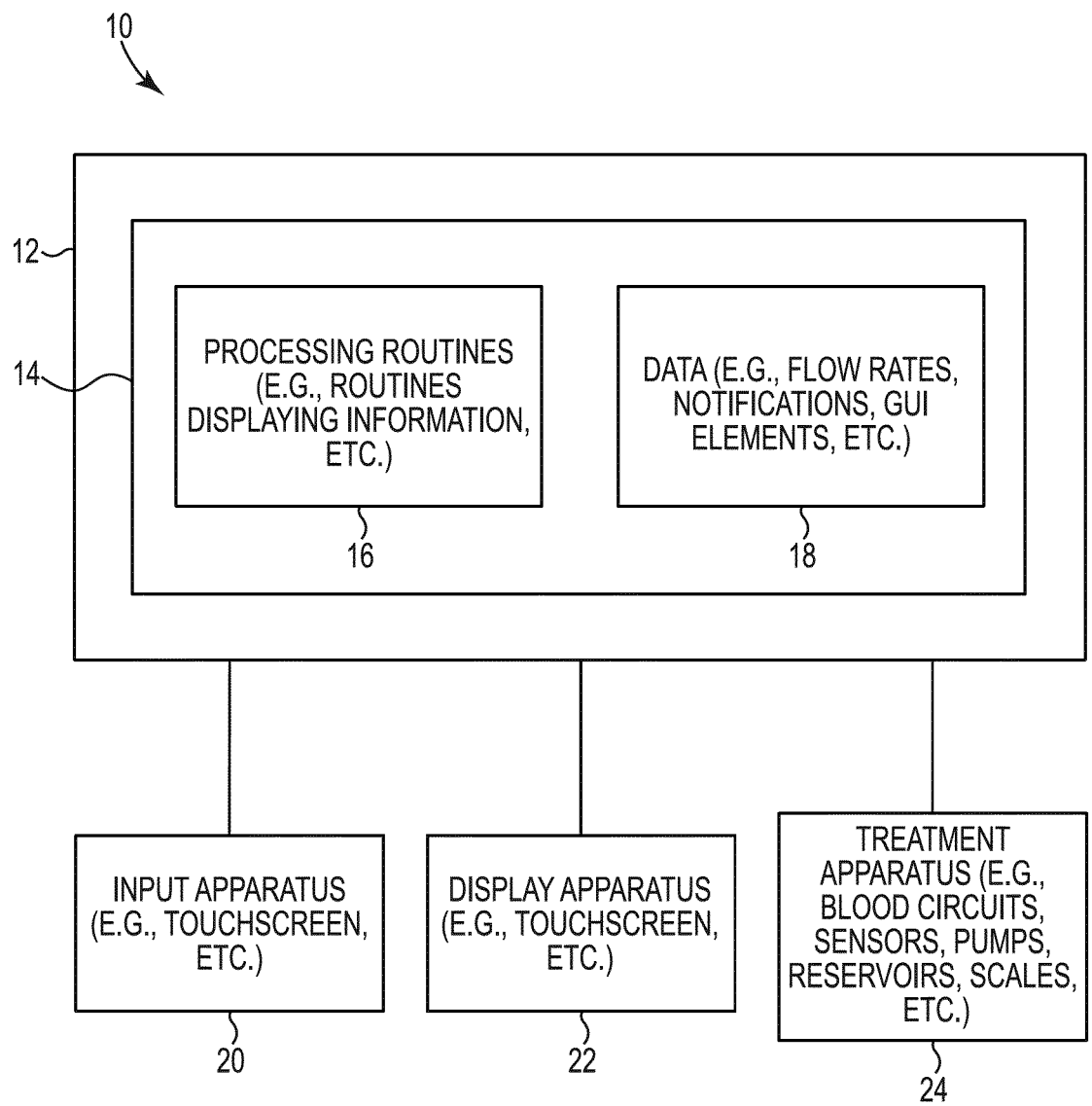
FIG. 1 is a block diagram of an exemplary medical treatment system including input apparatus, display apparatus, and treatment apparatus that may utilize the graphical user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary graphical user interface systems and methods for use with medical treatment apparatus such as, e.g., extracorporeal blood treatment apparatus, shall be described with reference to FIGS. 1-7. It will be apparent to one skilled in the art that elements or processes from one embodiment may be used in combination with elements or processes of the other embodiments, and that the possible embodiments of such graphical user interface systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and/or methods may provide, or include, graphical user interfaces (e.g., user-interactable graphical user interfaces, graphical user interfaces depicted on single-touch or multi-touch touchscreens, etc.) that include, or depict, a plurality of graphical elements, graphical regions, and graphical areas configured to provide information regarding one or more processes (e.g., one or more processes of an extracorporeal blood treatment system, etc.) and allow a user to adjust one or more parameters, or values, with respect to the one or more processes. In particular, the graphical user interfaces may include a blood circuit pressure graphical element configured to convey blood circuit pressure information such as present venous and arterial blood circuit pressures and past venous and arterial blood circuit pressures to a user. Further, the blood circuit pressure graphical element may be configured to allow a user to adjust alarm limits associated with each of the venous and arterial blood circuits. Still further, the positioning and appearance of the blood circuit pressure graphical element may further convey information to a user about the status of the extracorporeal blood treatment. For example, the blood circuit pressure graphical element may not be displayed when fluid (e.g., blood from a patient) is not flowing through either of the arterial or venous blood circuits of the extracorporeal blood treatment system. Further, for example, the blood circuit pressure graphical element may be located between a patient graphical element symbolically depicting a patient undergoing the extracorporeal blood treatment and a blood treatment graphical element corresponding to the treatment of the patient's blood to indicate that the blood circuit pressures are monitored from the venous and arterial blood circuits (e.g., between the blood treatment apparatus of the system performing the one or more blood treatment processes and the patient).

An exemplary extracorporeal blood treatment system 10 depicted in FIG. 1 may be used to execute, or perform, the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 (e.g., graphical regions, graphical elements, graphical areas, graphical animations, parameters, metrics, variables, images, values, limits, text strings, macros, etc.) that may be employed to perform, or carry out, exemplary methods and/or processes (e.g., displaying graphical user interfaces, allowing user interaction with graphical user interfaces, interpreting touch gestures on a touchscreen (e.g., swipes, drags, press-and-hold, touches, presses, etc.), displaying graphical elements, displaying graphs, displaying textual elements, displaying textual values, displaying status information, issuing alarms, running a treatment, determining problems with a treatment, exchanging/changing reservoirs, notifying operators/users of problems, etc.) for use in performing extracorporeal blood treatments. The computing apparatus 12 may be operatively coupled to the input apparatus 20 and the display apparatus 22 to, e.g., transmit data to and from each of the input apparatus 20 and the display apparatus 22. For example, the computing apparatus 12 may be operatively coupled to each of the input apparatus 20 and the display apparatus 22 using, e.g., analog electrical connections, digital electrical connections, wireless connections, bus-based connections, etc. As described further herein, an operator may provide input to the input apparatus 20 to manipulate, or modify, one or more graphical elements, graphical regions, and graphical areas displayed on the display apparatus 22 to, e.g., initiate one or more actions and/or processes related to the extracorporeal blood treatment system, indicate one or more actions and/or statuses related to one or more processes of the extracorporeal blood treatment system, etc.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may overlay the display apparatus 22 such that, e.g., an operator may use the touchscreen to interact (e.g., by touch) with a graphical user interface displayed on the display apparatus 22. For example, the input apparatus 20 may allow an operator to interact with a graphical user interface including an operation region containing, or depicting, graphical elements, graphical regions, and graphical areas associated with and representative of (or corresponding to) one or more features or processes of the extracorporeal blood treatment system when used in conjunction with the display apparatus 22 (e.g., displaying the graphical user interface). Further, more specifically, the input apparatus 20 may allow an operator to interact with a graphical user interface including to view various blood circuit pressure information and/or adjust one or more alarm limits with respect to the various blood circuit pressure information when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more graphical regions, graphical elements, and graphical areas.

For example, the graphical user interface displayed by the display apparatus 22 may include, or display, an operation region that may include multiple graphical regions, graphical areas, and graphical elements related to the extracorporeal blood treatment system. One or more graphical elements may correspond to the blood circuit pressures of the extracorporeal blood treatment system. More specifically, a graphical element may include one or more regions, areas, and/or elements corresponding to, related to, and/or representative of venous and arterial blood circuit pressures. Further, a graphical element, or region, may correspond to the extracorporeal blood treatment itself, and another graphical element, or area, may be correspond to the patient being treated using the extracorporeal blood treatment system. Each of these graphical regions, areas, and/or elements may be used by an operator to view information and/or modify one or more parameters, or values, of the extracorporeal blood treatment system.

Further, each graphical region, area, and/or element may correspond to one or more physical parts or portions (e.g., blood circuit, dialysate circuit, ultrafiltration circuit, blood connections to patient, etc.) of an exemplary extracorporeal blood treatment system. For example, moving (e.g., dragging-and-connecting) a graphical region, area, or element to another graphical region, area, or element may correspond to a physical part of the treatment system being physically coupled to another part of the treatment system and/or may execute physical, operatively coupling of physical parts of the treatment system. In other words, the graphical regions, areas, and/or elements described herein may be related to, associated with, and/or representative of one or more physical parts or portions of an exemplary extracorporeal blood treatment system, and manipulating (e.g., moving, selecting, etc.) the graphical regions, areas, and/or elements may affect, or be reflective of, the physical parts or portions of the system. Additionally, it may be described that the graphical regions, areas, and/or elements are "linked" to the physical parts or portions of an exemplary extracorporeal blood treatment system. Likewise, physical manipulation (e.g., physically moving, physically disconnecting/connecting, physically touching, etc.) of one or more parts or portions of an exemplary extracorporeal blood treatment system may affect the one or more graphical regions, areas, and/or elements corresponding to the physically manipulated parts or portions. For example, disconnecting a patient from a blood circuit may automatically initiate the movement of a patient graphical element about the graphical user interface (e.g., away from a blood treatment or blood circuit pressure graphical element).

As used herein, a "region" of a graphical user interface may be defined as a portion of the graphical user interface within which information may be displayed or functionality may be performed. Regions may exist within other regions, which may be displayed separately or simultaneously. For example, smaller regions may be located within larger regions, regions may be located side-by-side, etc.

Additionally, as used herein, an "area" of a graphical user interface may be defined as a portion of the graphical user interface located within a region that is smaller than the region within which the area is located. Still further, as used herein, an "element" of a graphical user interface may be defined as a component of the graphical user interface that may be located within, or adjacent to, a region, an area, or another element. In one or more embodiments, an "element" of a graphical user interface may include a perimeter, or border, defining the outer edge, or boundary, of the element. In one or more embodiments, an "element" of a graphical user interface is a defined, finite portion, item, and/or section of a graphical user interface.

The processing programs or routines 16 may include programs or routines for performing computational mathematics, touchscreen gesture interpretation algorithms, process performance algorithms, process automation algorithms, matrix mathematics, standardization algorithms, comparison algorithms, or any other processing required to implement one or more exemplary methods and/or processes described herein. Data 18 may include, for example, variables, graphics (e.g., graphical elements, graphical areas, graphical regions, icons, buttons, windows, dialogs, pull-down menus, 3D graphics, images, animations, etc.), graphical user interfaces, alarm data, fluid data, flow rates, fluid volumes, notifications, pressures, pressure limits, blood flow, blood flow limits, fluid removal rates, fluid removal limits, target blood temperatures, blood temperature limits, heuristics indicative of malfunction, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, or code, e.g., a high level procedural and/or object orientated programming language or code that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by a processor, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., blood circuits, sensors, pumps, reservoirs, scales, treatment sets, filters, pressure sensors, etc. For example, the treatment apparatus 24 may include a venous blood circuit configured to return blood to a patient from the treatment system and an arterial blood circuit configured to withdraw blood from the patient to be treated by the treatment system. Further, for example, the treatment apparatus 24 may include one or more sensors configured to measure, or monitor, the pressures inside of the venous blood circuit and arterial blood circuit. More specifically, the treatment apparatus 24 may include a venous blood circuit pressure sensor configured to measure, or monitor, the pressure inside of the venous blood circuit and an arterial blood circuit pressure sensor configured to measure, or monitor, the pressure inside of the arterial blood circuit. Still further, for example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may include systems such as, e.g., dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body via an arterial blood circuit and exposed to a treatment device to separate substances therefrom and/or to add substances thereto, and is then returned to the body via a venous blood circuit. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular treatment system.

Figure 2:
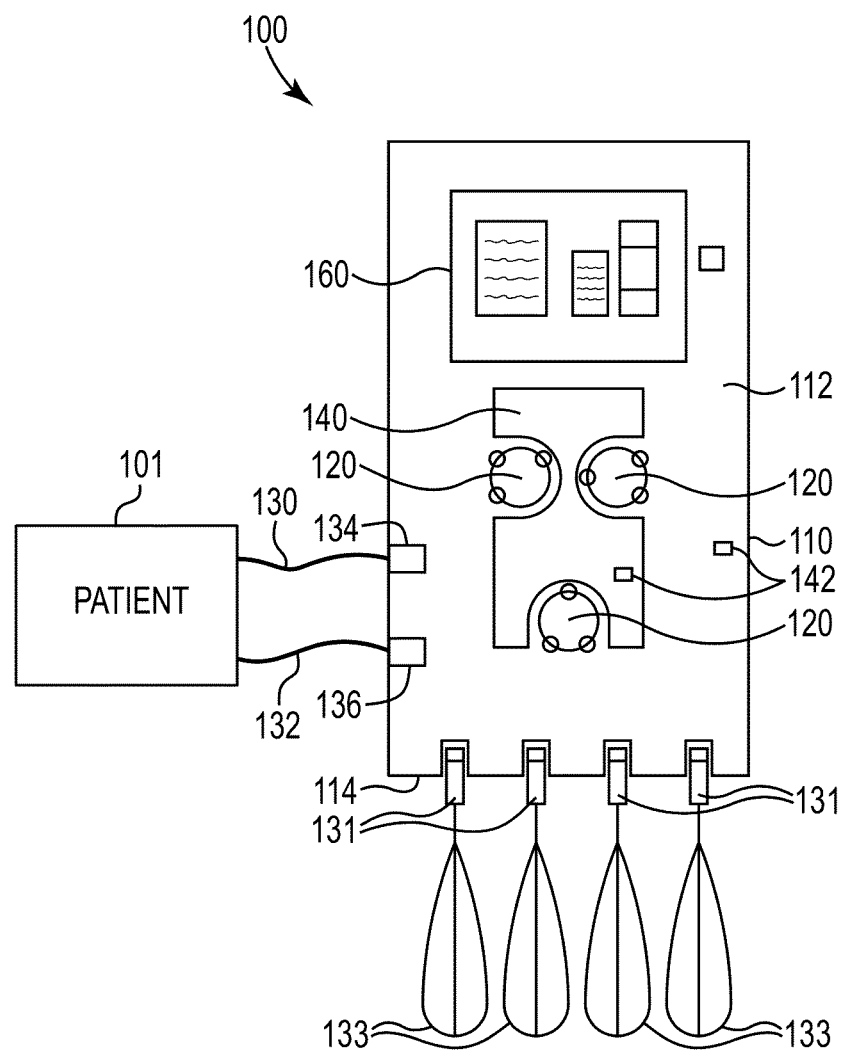
FIG. 2 is an illustration of an exemplary extracorporeal blood treatment system that may include graphical user interfaces as described herein.

Referring to FIG. 2, one illustrative embodiment of an extracorporeal blood treatment system, or apparatus, 100 is depicted. The system 100 includes a housing 110 having a front face 112. The system 100 further includes one or more pumps 120, one or more disposable elements, or integrated modules, 140, and one or more sensors 142 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc. The one or more disposable elements, or integrated modules, 140 (as depicted, a single disposable element 140) may be coupled to the system 100 to, e.g., provide at least a portion of the extracorporeal blood treatment fluid circuit that may be operatively coupled to one or more other fluid circuits, one or more pumps 120, and one or more sensors 142 of the system 100 for use in performing extracorporeal blood treatments. As shown, the one or more disposable elements 140 may be coupled to the front face 112 of the housing 110 of the system 100 to, e.g., integrate with the one or more other fluid circuits, pumps 120, and sensors 142 of the system 100.

The one or more disposable elements 140 may be described as including one or more disposable fluid circuits (e.g., an extracorporeal blood treatment circuits) and one or more blood treatment units operatively coupled to the one or more disposable fluid circuits. The blood treatment units may be, for example, a plasma filter, a hemodialysis filter, a hemofiltration filter, etc. Generally, the blood treatment units may be referred to as "filter."

As described herein, the system 100 may further include one or more sensors 142. As shown, two sensors 142 are identified on the system 100. One sensor 142 is located on, or coupled to, the front surface 112 of the housing 110 and another sensor 142 is located on the, or coupled to, the disposable element 140.

Additionally, the system 100 may include sensors 142 that are not visible on the outside of the housing 110, and instead, may be internal to the system 100 (e.g., within the housing 110). Generally, the system 100 may include any one or more sensors 142 so as to be able to monitor any value (e.g., any aspect, setting, level, condition, event internal to the system 100, etc.) of any process feature of the system 100 such as, e.g., process features during the performance of one or more extracorporeal blood treatments. For example, the system 100 may include one or more pressure sensors operable to measure, or monitor, various pressures of various circuits, chambers, pods, reservoirs, etc. of the system 100, e.g., during the performance of an extracorporeal blood treatment, during the performance of a pre-treatment process, during the performance of a disinfection, post-treatment process, etc. Further, for example, the system 100 may include one or more flow rate sensors operable to measure, or monitor, various fluid flow rates of fluids within various circuits, chambers, pods, reservoirs, etc. of the system 100, e.g., during the performance of an extracorporeal blood treatment, during the performance of a pre-treatment process, during the performance of a disinfection, post-treatment process, etc. Specifically, the system 100 may include one or more blood flow rate sensors to monitor various blood flow rates throughout the blood circuits of the system 100. Still further, for example, the system 100 may include other sensors 142 such as fluid level sensors, temperature sensors, leak detection sensors, etc. that may be used before an extracorporeal blood treatment is performed, during the performance of an extracorporeal blood treatment, and/or after an extracorporeal blood treatment is performed.

Additionally, the extracorporeal blood treatment fluid circuit of the system 100 may be described as being completed by a combination of the disposable element 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

The extracorporeal blood treatment system 100 may also include reservoir sensors, or scales, 131 (e.g., weight sensors, load cells, etc.), each of which is configured to hold and weigh a reservoir 133. The reservoir sensors 131 are positioned below a bottom end 114 of the housing 110, at least in part because the reservoirs 133 are typically attached to and hang from the reservoir sensors 131. Although the depicted embodiment of the extracorporeal blood treatment system 100 includes four reservoir sensors, or scales, 131 and associated reservoirs 133, alternative embodiments of extracorporeal blood treatment systems as described herein may include one or more reservoir sensors 131 and associated reservoirs 133 such as, e.g., as few as two reservoirs sensors 131 and associated reservoirs 133, four or more reservoirs sensors 131 and associated reservoirs 133, etc.

The extracorporeal blood treatment system 100 further includes a venous blood circuit 130 extending from a patient 101 (symbolically represented in FIG. 2) to the housing 110 to return blood to the patient 101 after the blood is treated by the system 100, an arterial blood circuit 132 extending from the patient 101 to the housing 110 to withdraw blood from the patient 101 for treatment, a venous blood circuit pressure sensor 134 configured to measure, or monitor, the pressure of the venous blood circuit 130 (e.g., the pressure of the blood, or fluid, within the venous blood circuit 130), and an arterial blood circuit pressure sensor 136 configured to measure, or monitor, the pressure of the arterial blood circuit 132 (e.g., the pressure of the blood, or fluid, within the arterial blood circuit 132).

The extracorporeal blood treatment system 100 also includes a display 160 used to show, or convey, information to an operator or user. The display 160 may also serve as an input device if, e.g., the display 160 is in the form of a touchscreen (e.g., a user interactable graphical user interface, etc.). Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to the housing 110 (e.g., a top end of the housing 110).

As shown in FIG. 1 and as related to FIG. 2, the treatment apparatus 24 may be operatively coupled, or connected, to the computing apparatus 12. Among the treatment apparatus 24 operably coupled to the computing apparatus 12 are the pumps 120, blood circuits 130, 132, and blood circuit pressure sensors 134, 136 as shown in FIG. 2.

Exemplary graphical user interfaces, or portions thereof, for use in displaying information related to extracorporeal blood treatments, providing functionality to an operator for use in preparing and performing extracorporeal blood treatments and/or configuring or maintaining an extracorporeal blood treatment system are depicted in FIGS. 3-7. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touchscreen, and in such configuration, the input apparatus would also be the touchscreen.

Exemplary extracorporeal blood treatment systems may use, or utilize, a plurality of different graphical user interfaces. For example, some exemplary graphical user interfaces may be used during an extracorporeal blood treatment to monitor and/or adjust one or more parameters of the extracorporeal blood treatment. Further, for example, some exemplary graphical user interfaces may be used to setup, or prepare, an extracorporeal blood treatment.

Each exemplary graphical user interface of the exemplary extracorporeal blood treatment systems described herein may include one or more graphical elements, regions, and areas used to display information to a user. An operator may use input apparatus 20 of the exemplary extracorporeal blood treatment system 10 described herein with reference to FIG. 1 to select or manipulate graphical elements, regions, and areas of the exemplary graphical user interfaces of FIGS. 3-7. As used herein, when an operator "selects" or "interacts with" a graphical element, area, and/or region of the graphical user interface, it is to be understood that "selecting" or "interacting with" the graphical element, area, and/or region to perform one or more tasks or steps may be conducted in many different ways using many different types of input apparatus. For example, when the input apparatus includes a touch screen, an operator may select or interact with a graphical element, area, and/or region by "touching" the graphical region with their finger or using a pointing device such as a stylus. Further, for example, when the input apparatus includes a mouse or similar pointing device, an operator may select or interact with a graphical element, area, and/or region by locating an arrow or cursor over the desired graphical region "clicking" the graphical region. Still further, for example, when the input apparatus includes a series of buttons and/or knobs, an operator may select or interact with a graphical element, area, and/or region by using the buttons and/or knobs to navigate to the graphical region and to select it (e.g., by depressing the button and/or knob). Additionally, it is to be understood that selection of or interaction with a graphical element, area, and/or region may be conducted using various gestures such as, for example, but not limited to, swipes, select-and-drag, press, tracing of various shapes, pinch-inwardly, pinch-outwardly, finger spread, multi-finger touches and/or swipes, etc.

An exemplary graphical user interface 200 is depicted in FIGS. 3A-3F that may be generally used to perform at least a portion of an extracorporeal blood treatment. As shown, the graphical user interface 200 may include a plurality of graphical regions that may be used in the preparation of an extracorporeal blood treatment as well as other functionality and/or processes of the extracorporeal blood treatment system. At least one of the graphical regions may be more specifically referred to as an operation region 201, which is located within (e.g., located centrally within) the exemplary graphical user interface 200.

The operation region 201 may include various graphical regions, areas, and elements that may be used to indicate, initiate, revert, and stop one or more process features of processes of the extracorporeal blood treatment system. In the exemplary graphical user interface 200, the operation region 201 includes a blood treatment graphical element 202 corresponding to (e.g., representative of, associated with, etc.) one or more processes to be performed during an extracorporeal blood treatment. The blood treatment graphical element 202 may include a plurality of process feature graphical areas such as, e.g., a blood process feature graphical area, dialysate process feature graphical area, and an ultrafiltration process feature graphical area. Further, the blood treatment graphical element 202 and any process feature graphical areas thereof may be described as being representative of the actual blood treatment itself.

Additionally, when a blood treatment is not being performed, such as during setup before a blood treatment is performed or during disinfection after a blood treatment is performed, another graphical element similar to the blood treatment graphical element 202 may be used during the treatment setup and disinfection.

Further, the operation region 201 of the exemplary graphical user interface 200 may include a patient graphical element 208 that is associated with and representative of the actual patient to be treated by the extracorporeal blood treatment system. As shown, the patient graphical element 208 may define a diagrammatic, or symbolic, representation of a human body. The patient graphical element 208 may define an outline, or perimeter, of the human body, or form, including a plurality of body parts or portions such as, e.g., two arms, two legs, a torso, a head, a neck, etc. As shown, the patient graphical element 208 appears to be in a standing or prone position. Further, the patient graphical element 208 may be recognizable by a user to represent the human patient to be treated by the system and/or undergoing an extracorporeal blood treatment performed by the system.

The exemplary extracorporeal blood treatment systems described herein may be described as including two blood circuits to be coupled to a patient: a venous blood circuit and an arterial blood circuit. The venous blood circuit may be described as the "return" blood circuit as it returns blood to the patient after the blood has been treated using the extracorporeal blood treatment system. The arterial blood circuit may be described as the "withdrawal" blood circuit as it withdraws blood from the patient to be treated using the extracorporeal blood treatment system.

Figure 3A:
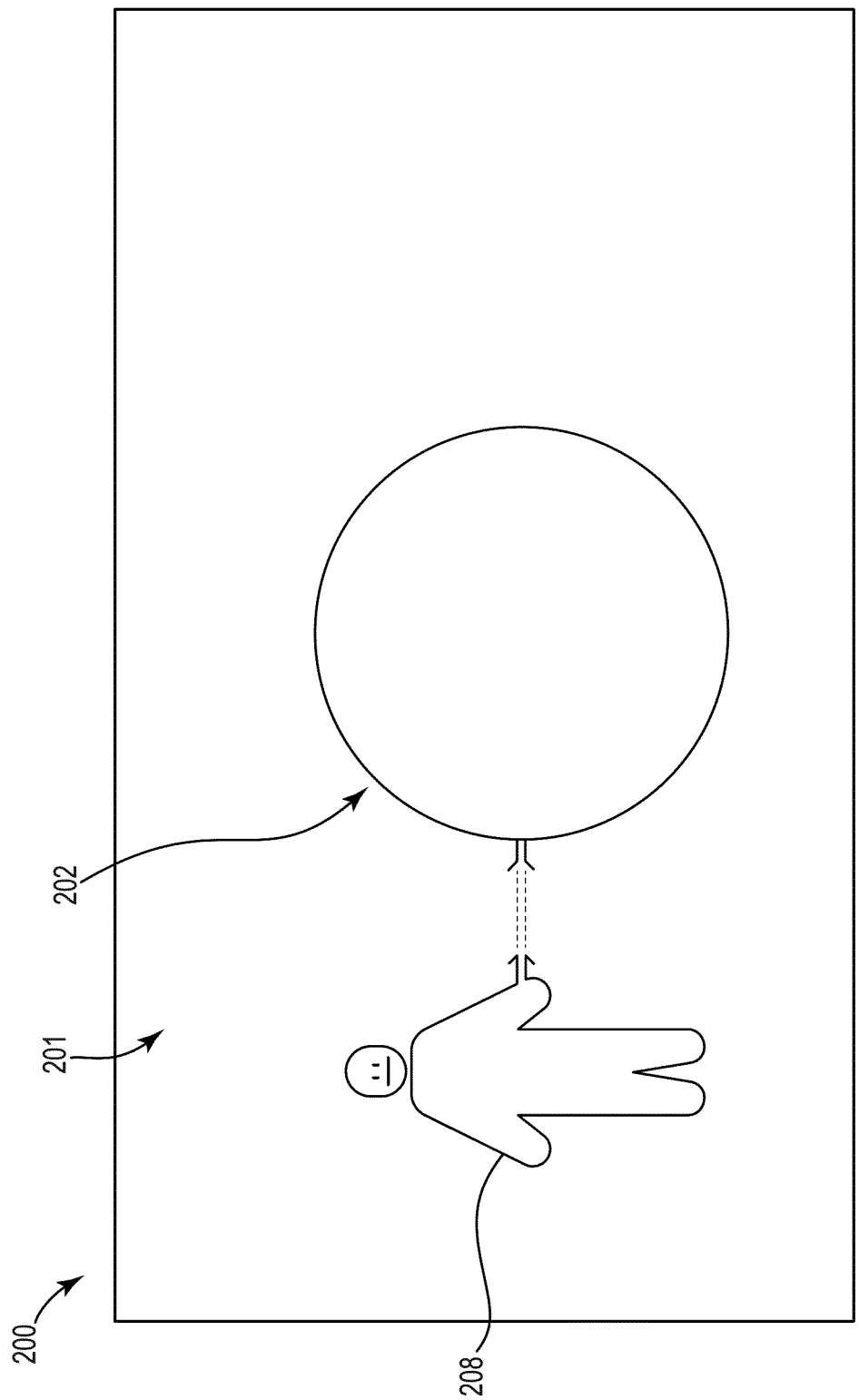
Figure 3B:
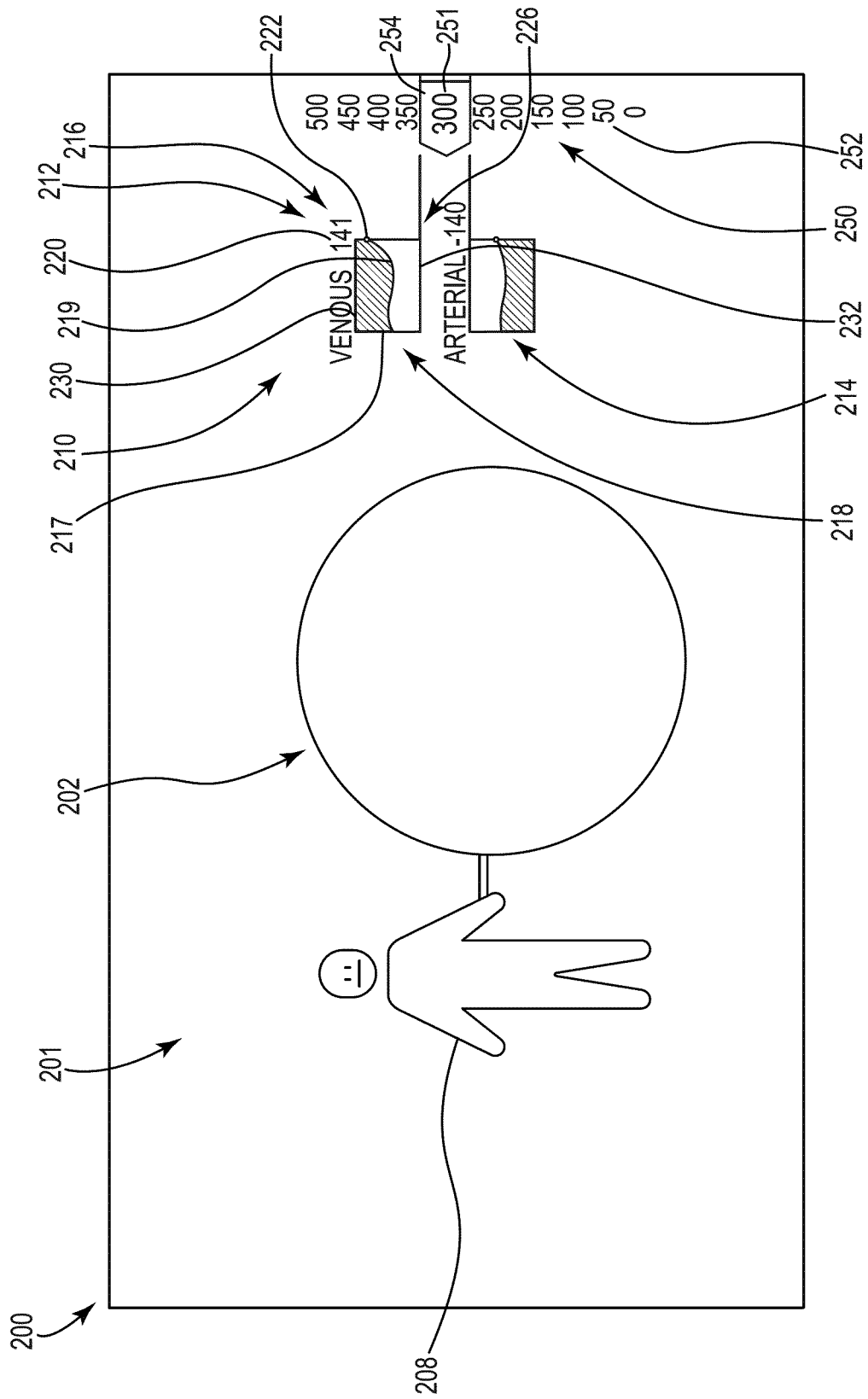

When the extracorporeal blood treatment system detects that a patient is connected to the system, the patient graphical element 208 may be automatically moved towards the blood treatment graphical element 202, or after the patient has been connected to the extracorporeal blood treatment, a user may move (e.g., selected-and-drag, swipe, etc.) the patient graphical element 208 towards the blood treatment graphical element 202 as shown in FIG. 3B.

After a patient has been connected to each of the venous and arterial blood circuits of the extracorporeal blood treatment system, a blood circuit pressure graphical element 210 may be depicted in the graphical user interface 200. In other words, the blood circuit pressure graphical element 210 may be displayed on the graphical user interface 200 in response to the patient being connected to the extracorporeal blood treatment system. For example, the blood circuit pressure sensors 134, 136 may detect blood in the blood lines 130, 132 and/or one or more other sensors of an exemplary extracorporeal blood treatment system may detect that a patient is connected to the system, and in response to detection of blood and/or patient connection, the blood circuit pressure graphical element 210 may be displayed on the graphical user interface 200. In other embodiments, the blood circuit pressure graphical element 210 may be displayed before the patient has been connected for use in setup or after the patient has been disconnected for use in disinfection.

The blood circuit pressure graphical element 210 may correspond to each of the venous and arterial blood circuits of the extracorporeal blood treatment system and may be broadly described as a graphical element configured to provide (e.g., depict, display, show, etc.) information with respect to each of the venous and arterial blood circuits 130, 132, to allow a user to view additional information with respect to each of the venous and arterial blood circuits 130, 132, and to allow a user to modify, or change, one or more parameters, or values, related to the venous and arterial blood circuits 130, 132.

The blood circuit pressure graphical element 210 may include a venous portion 212 corresponding to the venous blood circuit 130 and an arterial portion 214 corresponding to the arterial blood circuit 132. Each of the venous portion 212 and the arterial portion 214 may be similar to each other and include the same, or similar, functionality, and as such, only the venous portion 212 will be further described in detail to, e.g., reduce redundancy.

Figure 4A:
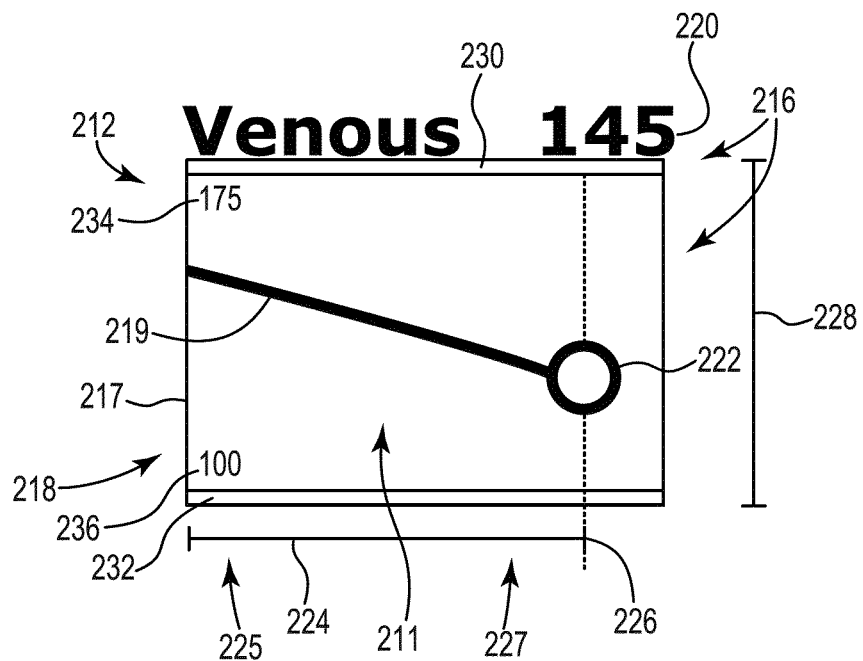
FIGS. 4A-4D depict a venous portion of an exemplary blood circuit pressure graphical element of the graphical user interface of FIGS. 3B-3F.

As shown in the venous portion 212 of the graphical user interface 200 of FIG. 3B and in the expanded view of the venous portion 212 of FIG. 4A, the venous portion 212 may include a presently-monitored venous blood circuit pressure value 216 and a graphical representation of previously-monitored venous blood circuit pressure values 218. In this example, the presently-monitored venous blood circuit pressure value 216 is represented alphanumerically 220 and graphically as a circle, or dot, 222 with respect to the graphical representation of previously-monitored venous blood circuit pressure values 218. In other embodiments, the presently-monitored venous blood circuit pressure value 216 may only be represented alphanumerically 220 and not graphically, or the presently-monitored venous blood circuit pressure value 216 may only be represented graphically, e.g., as a circle 222, and not alphanumerically 220. In the example depicted in FIG. 4A, the presently-monitored venous blood circuit pressure value 216 is 145 millimeters of mercury (mmHG), and in the example depicted in FIG. 3B, the presently-monitored venous blood circuit pressure value 216 is 141 mmHG.

In this embodiment, as shown in FIG. 4A, the graphical representation of previously-measured venous blood circuit pressure values 218 may include a venous blood circuit pressure line graph 217 plotting the previously-measured venous blood circuit pressure values 219 over a trailing time period 224 prior to the present 226 (represented by the dotted line). Further shown in FIG. 4A, the y-axis is the range 228 of venous blood circuit pressure values displayable, which in this example, is the range between the upper and lower venous blood circuit pressure alarm limit graphical elements 230, 232 described further herein. In the embodiment depicted in FIG. 4A, the present 226 (e.g., the current time) is not located on the rightmost boundary of the graph 217 and is, instead, located a distance away from the rightmost boundary of the graph. In the embodiment depicted in FIGS. 3B-3F, the present 226 is located on, or at, the rightmost boundary of the graph.

The trailing time period 224 of the graph 217 may be selectable by a user or preset by the system. The trailing time period 224 may be about 1 minute to about 5 hours. In at least some embodiments, the trailing time period 224 is greater than or equal to about 15 seconds, greater than or equal to about 30 seconds, greater than or equal to about 1 minute, greater than or equal to about 2 minutes, greater than or equal to about 5 minutes, greater than or equal to about 10 minutes, greater than or equal to about 15 minutes, greater than or equal to about 30 minutes, etc. In at least some embodiments, the trailing time period 224 is less than or equal to about 3 hours, less than or equal to about 2 hours, less than or equal to about 1.5 hours, less than about 1 hour, less than or equal to about 45 minutes, less than or equal to about 20 minutes, etc.

The trailing time period 224 of the graph 217 may be dynamic such that the trailing time period 224 increases as time passes and as more venous blood circuit pressure values are monitored and recorded. For example, when venous blood circuit pressure values have been recorded for the first twenty seconds, the trailing time period 224 may represent the entire twenty seconds thereby displaying twenty seconds of venous blood circuit pressure values 219, and when venous blood circuit pressure values have been recorded for the first sixty seconds, the trailing time period 224 may represent the entire sixty seconds thereby displaying sixty seconds of venous blood circuit pressure values 219. Thus, the trailing time period 224 will have adjusted from displaying twenty seconds to displaying sixty seconds of venous blood circuit pressure values 219. In other words, the trailing time period 224 may dynamically adjust depending on how much time has elapsed since, e.g., venous blood circuit pressure values began being monitored, the blood treatment began, etc.

In one or more embodiments, the trailing time period 224 of the graph 217 may be described as being a linear time period. A linear time period may be described as a time period that uses a uniform scale to display time. For example, each time "segment" along the x-axis may represent the same amount of time, and thus, the time indications, which may show the scale of the time axis, may be spaced uniformly along the axis to indicate a linear time period. In other words, time does not "speed up" or "slow down" when moving along the time axis in a linear time period.

Further, recently-monitored venous blood circuit pressure values may be more relevant or important to an operator than less recently-monitored venous blood circuit pressure values, and thus, the venous portion 212 of the blood circuit pressure graphical element 210 may be configured to display the recently-monitored venous blood circuit pressure values in more detail than the less recently-monitored venous blood circuit pressure values. To do so, in at least one embodiment, the trailing time period 224 of the graph 217 may not be a linear time period, and instead, may be a non-linear time period. A non-linear time period may be described as a time period that does not use a uniform scale to display time. For example, each time "segment" along the x-axis may represent a different, or varying, amount of time, and thus, the time indications, which may show the scale of the time axis, may be spaced differently along the axis to indicate a non-linear time period. In other words, time may "speed up" or "slow down" when moving along the time axis. For example, as labeled in FIG. 4A, a left portion 225 of the graph 217 may represent more time than a right portion 227 of the graph 217. In other words, time may be more compressed in the left portion 225 than the right portion 227 such that the left portion 225 of the graph 217 may graphically represent more venous blood circuit pressure values 219 than the right portion 227 of the graph 217. The right portion 227, however, will show more detail for the venous blood circuit pressure values 219 displayed in the right portion 227 because less venous blood circuit pressure values 219 will be plotted over the same or similar distance than the left portion 225. Thus, a user may glance, or view, the venous portion 212 of the blood circuit pressure graphical element 210 to ascertain a more detailed graphical representation 219 of recent previously-monitored venous blood circuit pressure values on the right side 227 of the graph 217 and a less detailed view but over a greater period of time of the less recent previously-monitored venous blood circuit pressure values on the left portion 225 of the graph 217.

For example, the previously-monitored venous blood circuit pressure values over the last 5 minutes (in other words, 5 minutes prior to the present) may be more important than the previously-monitored blood circuit pressure values over the last 55 minutes prior to the last 5 minutes. Thus, the last 5 minutes may extend over the right half of the graph 217 while the remainder of the graph 217 may represent 55 minutes.

The venous portion 212 of the blood circuit pressure graphical element 210 may further include an upper venous blood circuit pressure alarm limit graphical representation 230 indicative of an upper venous blood circuit pressure alarm limit value and a lower venous blood circuit pressure alarm limit graphical representation 232 indicative of a lower venous blood circuit pressure alarm limit value. The upper and lower venous blood circuit pressure alarm limit values may be the venous blood circuit pressure values at which an alarm is triggered. The upper and lower venous blood circuit pressure alarm limit values may be alphanumerically depicted proximate the upper and lower venous blood circuit pressure alarm limit graphical representations, respectively, which may be referred to as upper and lower venous blood circuit pressure alarm limit alphanumeric representations 234, 236, respectively. When an alarm is triggered, the system may provide a notification to a user such as, e.g., one or more sounds, lights, messages, etc.

In other words, the upper and lower venous blood circuit pressure alarm limit values may define a range within which the presently-monitored venous blood circuit pressure value may be located without triggering an alarm. When the presently-monitored venous blood circuit pressure value falls outside, or is located outside, the range defined by the upper and lower venous blood circuit pressure alarm limit values, an alarm may be triggered.

In these examples, the upper venous blood circuit pressure alarm limit graphical representation 230 is the upper boundary of the graph 217 of the graphical representation of the previously-monitored venous blood circuit pressure values 218, and the lower venous blood circuit pressure alarm limit graphical representation 232 is the lower boundary of the graph 217 of the graphical representation of the previously-monitored venous blood circuit pressure values 218. The upper and lower venous blood circuit pressure alarm limit graphical representations 230, 232 may graphically indicate a quantitative difference between the presently-monitored venous blood circuit pressure value 216 and the upper and lower venous blood circuit pressure alarm limit values. As such, a user may be able to view the blood circuit pressure graphical element 210 to ascertain the presently-monitored venous blood circuit pressure value 216, previously-monitored venous blood circuit pressure values, and where such monitored venous blood circuit pressure values are and have been located with respect to the upper and lower venous blood circuit pressure alarm limit values.

Figure 4B:
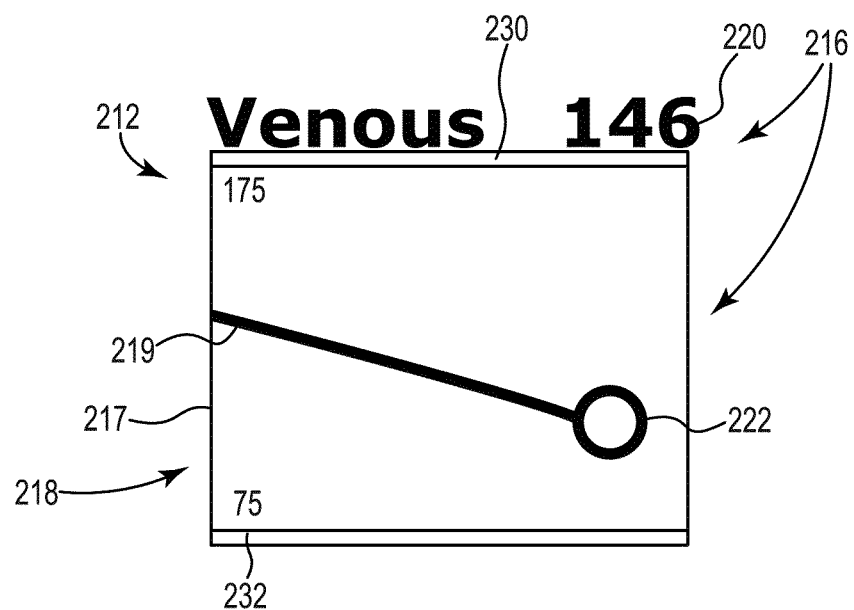

The upper venous blood circuit pressure alarm limit value and the lower venous blood circuit pressure alarm limit value may be adjustable by a user using the venous portion 212 of the blood circuit pressure graphical element 210 in various ways. For example, a user may adjust the upper venous blood circuit pressure alarm limit value by selecting and moving the upper venous blood circuit pressure alarm limit graphical representation 230, and may adjust the lower venous blood circuit pressure alarm limit value by selecting and moving the lower venous blood circuit pressure alarm limit graphical representation 232. More specifically, a user may select-and-drag (e.g., touch and, without breaking contact from a touchscreen, move) one of the upper or lower venous circuit pressure alarm limit graphical representations 230, 232 upwardly to increase or downwardly to decrease the venous circuit pressure alarm limit value associated therewith. A user may decrease the lower venous circuit pressure alarm limit value from 100 mmHG as shown in FIG. 4A to 75 mmHG as shown in FIG. 4B. Further, as shown in FIG. 4B, the range of displayable venous blood circuit pressure values may be increased in size (e.g., the y-axis range may increase) in response to a decreased lower venous blood circuit pressure alarm limit.

Further, for example, a user may adjust the upper or lower venous blood circuit pressure alarm limit values by selecting the upper venous blood circuit pressure alarm limit graphical representation 230 or the lower venous blood circuit pressure alarm limit graphical representation 232, respectively, to display an venous blood circuit pressure alarm limit value entry dialog within which a user may enter a numerical value for the upper or lower venous blood circuit pressure alarm limit value. In other words, selection of either of the upper or lower venous blood circuit pressure alarm limit graphical representations 230, 232 may "pop-up" a graphical region, area, or element configured to allow a user to enter a new upper or lower venous blood circuit pressure value.

Figure 4C:
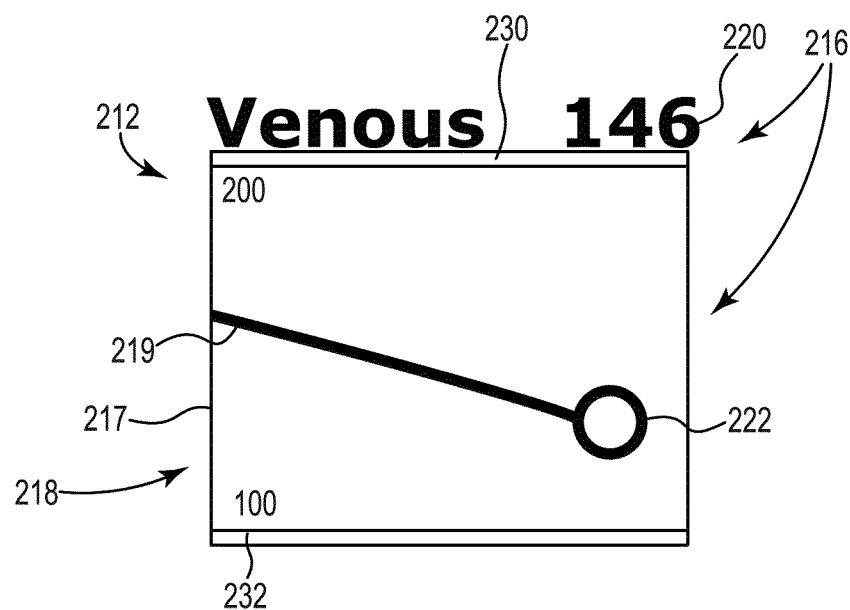

Both of the upper and lower venous blood circuit pressure alarm limits may be changed at the same time or simultaneously. For example, a user may simultaneously adjust both the upper and lower venous blood circuit pressure alarm limit values by selecting (e.g., touching) at least a portion the venous portion 212 of the blood circuit pressure graphical element (e.g., by selecting-and-holding a central region 211 of the venous portion 212, etc.) to simultaneously select each of the upper and lower venous blood circuit pressure alarm limit graphical representations 230, 232 such that the user may move, or drag, the selected portion of the venous portion 212 upwardly to simultaneously increase both of the upper and lower venous circuit pressure alarm limit values and downwardly to simultaneously decrease both of the upper and lower venous circuit pressure alarm limit values. In other words, the upper and lower venous blood circuit pressure graphical representations 230, 232 may represent a slideable window, or range, of acceptable venous blood circuit pressure values that may be selected and moved, or slid, by a user. As shown in FIG. 4C, a user has simultaneously increased both of the upper and lower venous circuit pressure alarm limit values from 175 mmHG and 75 mmHG, respectively, to 200 mmHG and 100 mmHG.

Figure 4D:
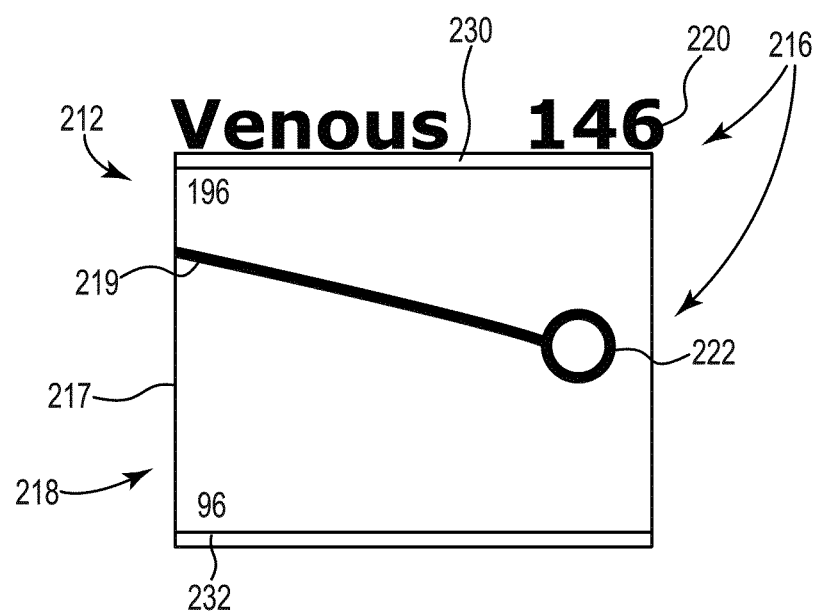

Further, for example, a user may simultaneously adjust both the upper and lower venous blood circuit pressure alarm limit values by selecting (e.g., touching) at least a portion of the venous portion 212 of the blood circuit pressure graphical element 210 (e.g., by double-tapping a central region 211 of the venous portion 212, etc.) to automatically adjust the upper and lower venous blood circuit pressure alarm graphical elements 230, 232, and associated venous blood circuit pressure alarm limits, to be equidistant from the presently-monitored venous blood circuit pressure value 216 without adjusting the length of the range of blood circuit values 228 (e.g., the y-axis of the graph). In other words, the upper and lower venous blood circuit pressure alarm graphical elements 230, 232, and associated venous blood circuit pressure alarm limit values, may be centered around the presently-monitored venous blood circuit pressure value 216 by a user selecting at least a portion of the venous portion 212 (e.g., by double-tapping a central region 211 of the venous portion 212, etc.). As shown in FIG. 4D, a user has simultaneously "centered" both of the upper and lower venous circuit pressure alarm limit values about the presently-monitored venous blood circuit pressure value 216 that is 146 mmHG such that the upper and lower venous circuit pressure alarm limit values are 196 mmHG and 96 mmHG, respectively.

In one or more embodiments, the venous circuit pressure alarm limit graphical representations 230, 232 may only be displayed when the presently-measured venous blood circuit pressure value 216 is within a selected value, or range, of the venous circuit pressure alarm limit values associated with the venous circuit pressure alarm limit graphical representations 230, 232. In other words, the venous circuit pressure alarm limit graphical representations 230, 232 may not be displayed unless, or until, the presently-measured venous blood circuit pressure value 216 is within a selected value, or range, of the venous circuit pressure alarm limit values associated with the venous circuit pressure alarm limit graphical representations 230, 232. Additionally, in at least this embodiment, when the venous circuit pressure alarm limit graphical representations 230, 232 are not displayed, the upper and lower venous blood circuit pressure alarm limit alphanumeric representations 234, 236 are also not displayed. In other embodiments, venous blood circuit pressure alarm limit alphanumeric representations 234, 236 may be displayed even when the venous circuit pressure alarm limit graphical representations 230, 232 are not displayed.

Figure 5A:
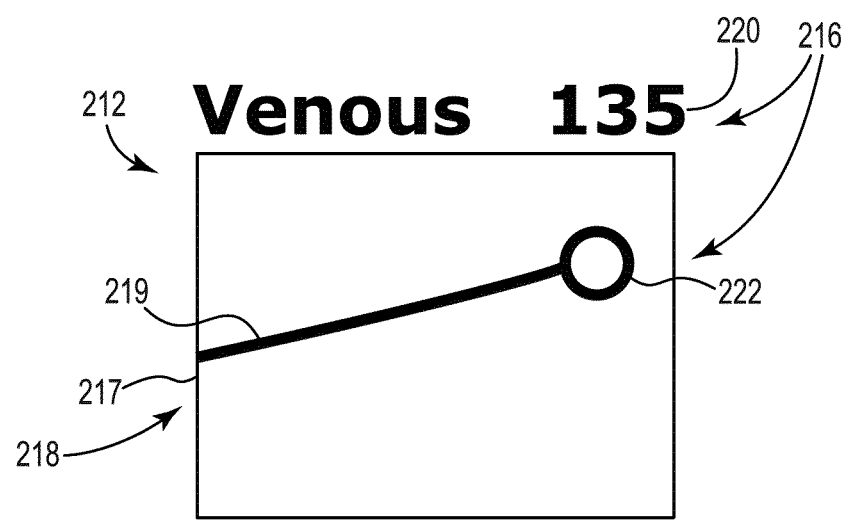
FIGS. 5A-5B depict a venous portion of an exemplary blood circuit pressure graphical element of the graphical user interface of FIGS. 3B-3F.
Figure 5B:
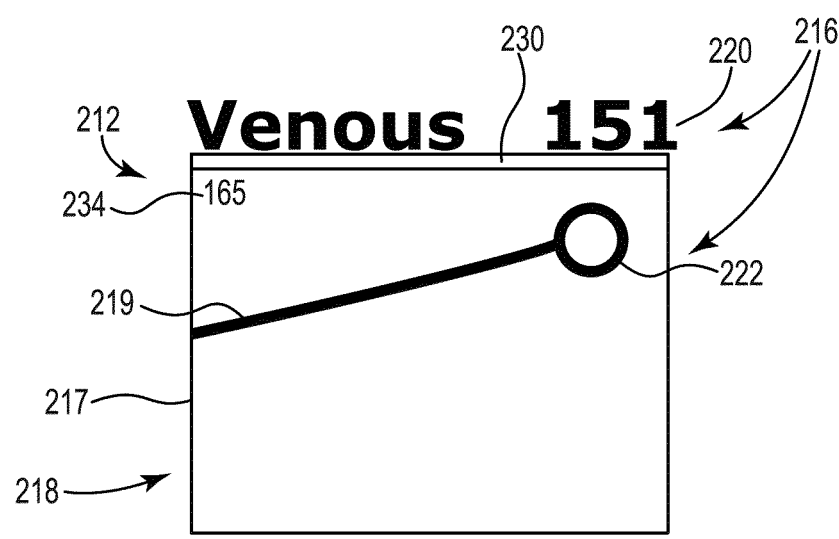

For example, as shown in FIG. 5A, the venous portion 212 does not include upper and lower venous blood circuit pressure alarm limit graphical representations 230, 232. After the presently-monitored venous blood circuit pressure value 216 increases beyond 150 mmHG as shown in FIG. 5B, the upper venous blood circuit pressure alarm limit graphical representations 230 is displayed because the presently-monitored venous blood circuit pressure value 216, 151 mmHG, has increased to within 15 mmHG of the upper venous blood circuit pressure alarm limit value, which is 165 mmHG. As such, in this embodiment, the selected value, or range, for triggering, or initiating, the display of the venous blood circuit pressure alarm limit graphical representations 230, 232 is 15 mmHG. In other embodiments, the selected value, or range, for triggering, or initiating, the display of the venous blood circuit pressure alarm limit graphical representations 230, 232 may be less than 15 mmHG or more than 15 mmHG. For example, the selected value for initiating the display of the venous blood circuit pressure alarm limit graphical representations 230, 232 may be greater than or equal to about 2 mmHG, greater than or equal to about 5 mmHG, greater than or equal to about 7 mmHG, greater than or equal to about 10 mmHG, greater than or equal to about 12 mmHG, greater than or equal to about 15 mmHG, etc. Further, for example, the selected value for initiating the display of the venous blood circuit pressure alarm limit graphical representations 230, 232 may be less than or equal to about 30 mmHG, less than or equal to about 25 mmHG, less than or equal to about 20 mmHG, less than or equal to about 17 mmHG, less than or equal to about 14 mmHG, less than or equal to about 11 mmHG, etc.

The blood circuit graphical element 210 may be positioned, or located, about the graphical user interface 200 to provide various functionality and/or to indicate various information to a user. For example, in FIG. 3B, the blood circuit graphical element 210 is located proximate a blood flow rate area 250. The blood flow rate area 250 may depict, or display, the present, or current, blood flow rate value 251, which in this example, is 300 milliliters per minute (mL/min), a blood flow rate scale 252, and a blood flow rate adjustment graphical element 254. The blood flow rate adjustment graphical element 254 may be used by a user to adjust the blood flow rate value 251 of the extracorporeal blood treatment being performed by the extracorporeal blood treatment system (e.g., the system may adjust the rate at which the pumps are operating to perform the treatment, etc.). For example, a user may select-and-drag the blood flow rate adjustment graphical element 254 upwardly along the scale 252 to increase the blood flow rate and downwardly along the scale 252 to decrease the blood flow rate. It is to be understood that the blood flow rate area 250 including the blood flow rate adjustment graphical element 254 and other parts, or portions, thereof as shown in FIGS. 3B-3F is only one example, and that other embodiments may depicted an exemplary blood flow rate area including a blood flow rate adjustment graphical element and other parts, or portions, thereof in many different ways. For example, as will be described further herein with respect to FIGS. 6A-6B, an exemplary blood flow rate area may be depicted as a circular, "dial"-type graphical element including a blood flow rate adjustment graphical element (e.g., a pointer, a clock hand, etc.) that indicates the present blood flow rate by "pointing at" the present blood flow rate located around the dial. Further, for example, in other embodiments, a blood flow rate area may include one or more dials, up/down buttons, or elements, sliders, etc.

The blood circuit pressure graphical element 210, or one or more portions thereof, may be graphically emphasized in response to, or triggered by, one or more system-initiated (e.g., initiated automatically) or user-initiated events to, e.g., draw the attention of a user. For example, the blood circuit pressure graphical element 210, or one or more portions thereof, may move about the graphical user interface 200 (e.g., movement of the blood circuit pressure graphical element with the blood flow rate adjustment graphical element), change color, be highlighted, change graphical size, become animated, flash, and/or blink in response to, or triggered by, one or more system-initiated or user-initiated events such as, e.g., a blood flow rate adjustment, an alarm (e.g., which automatically triggers, or initiates, the emphasization), etc. Additionally, other portions, regions, areas, and elements of the graphical user interface 200 other than the blood circuit pressure graphical element 210, or one or more portions thereof, or the remainder of the graphical user interface 200, may be graphically de-emphasized in response to the emphasis of the blood circuit pressure graphical element 210 to, e.g., further graphically emphasize the blood circuit pressure graphical element 210. The de-emphasization may include graying-out, de-colorizing, tinting, low-lighting, etc. the remainder of the graphical user interface 200.

Figure 3C:
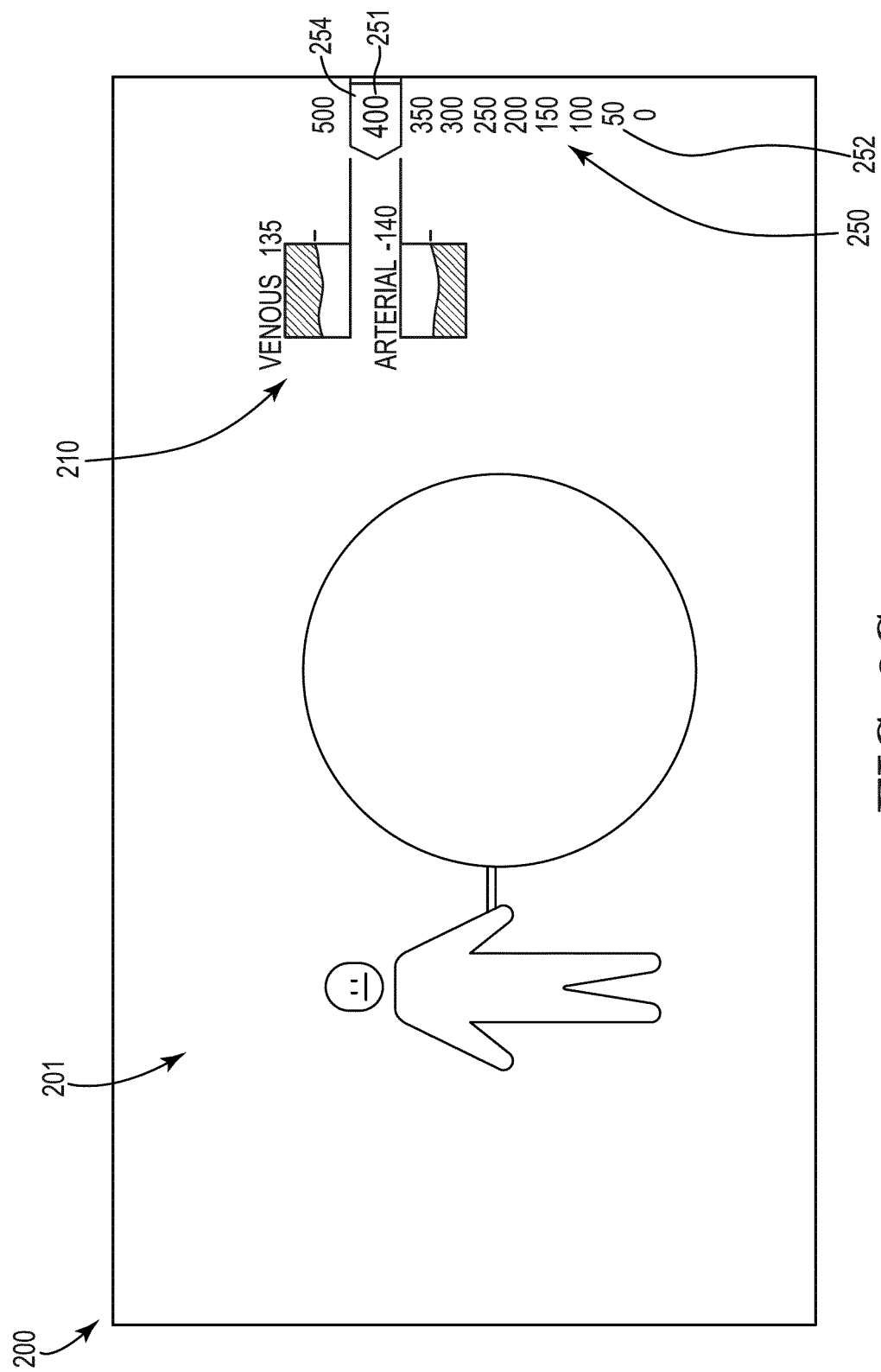

In this example, the blood circuit pressure graphical element 210, which is located in proximity with the blood flow rate adjustment graphical element 254, may be configured to move with the blood flow rate adjustment graphical element 254 when the blood flow rate adjustment graphical element 254 is moved to adjust the blood flow rate value 251. In other words, the graphical emphasis of the blood circuit pressure graphical element 210 in response to the blood flow rate being adjusted using the blood flow rate adjustment graphical element 254 may be the movement of the blood circuit pressure graphical element 210 with the blood flow rate adjustment graphical element 254. For example, as shown in FIG. 3C, a user has moved the blood flow rate adjustment graphical element 254 upwardly to adjust the blood flow rate value 251 from 300 mL/min to 400 mL/min and the blood circuit pressure graphical element 210 has moved upwardly with the blood flow rate adjustment graphical element 254.

In other words, the blood circuit pressure graphical element 210 may be located closer to the blood flow rate area 250, and in particular, the blood flow rate adjustment graphical element 254 than other regions, areas, and graphical elements of the graphical user interface 200. Further, the blood circuit pressure graphical element 210 may be described as being associated with the blood flow rate area 250 such that the blood circuit pressure graphical element 210 may be described as a graphical element of the blood flow rate area 250. As such, the blood flow area 250 may be described as including the blood circuit pressure graphical element 210 and the blood flow rate adjustment graphical element 254, both of which are located along the blood flow rate scale 252.

The positioning of the blood circuit pressure graphical element 210 in proximity to, or as part of, the blood flow rate area 250 may provide an indication to a user that the venous and arterial blood circuit pressures of the blood circuit pressure graphical element 210 are associated and linked to the blood flow rate of the extracorporeal blood treatment. Further, at least in some instances, the adjustment of the blood flow rate value 251 may affect the venous and arterial blood circuit pressure values, and as such, the location and positioning of the blood circuit pressure graphical element 210 in proximity to, or as part of, the blood flow rate area 250 may indicate to a user that adjustment of the blood flow rate value 251 may affect the venous and arterial blood circuit pressure values and may further allow a user to immediately see, or recognize, the effects that an adjusted blood flow rate may have on the venous and arterial blood circuit pressure values as provided by the blood circuit pressure graphical element 210.

Figure 6A:
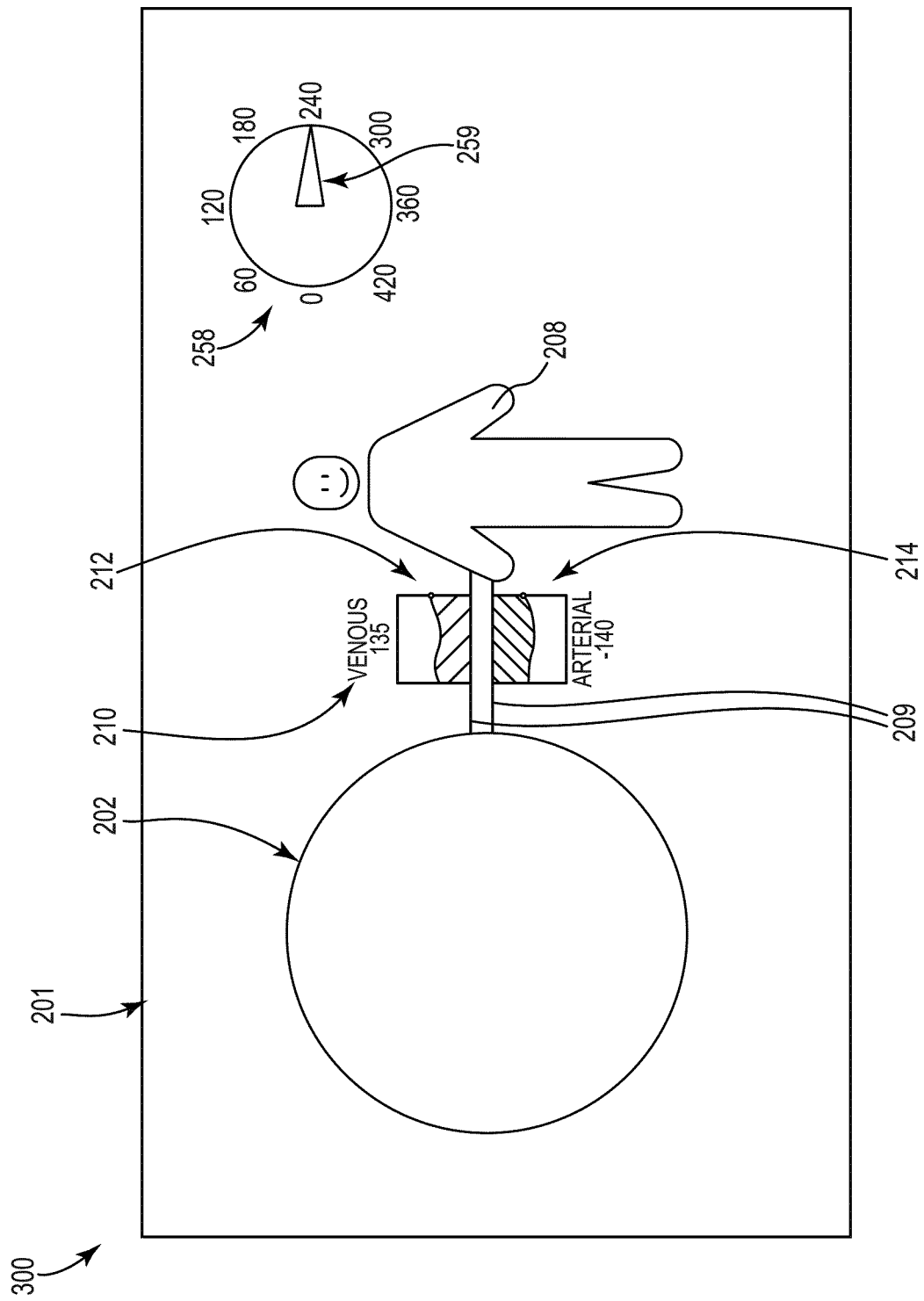
FIGS. 6A-6B depict exemplary graphical user interfaces including a blood circuit pressure graphical element for use in an extracorporeal blood treatment system such as, for example, shown generally in FIGS. 1-2.
Figure 6B:
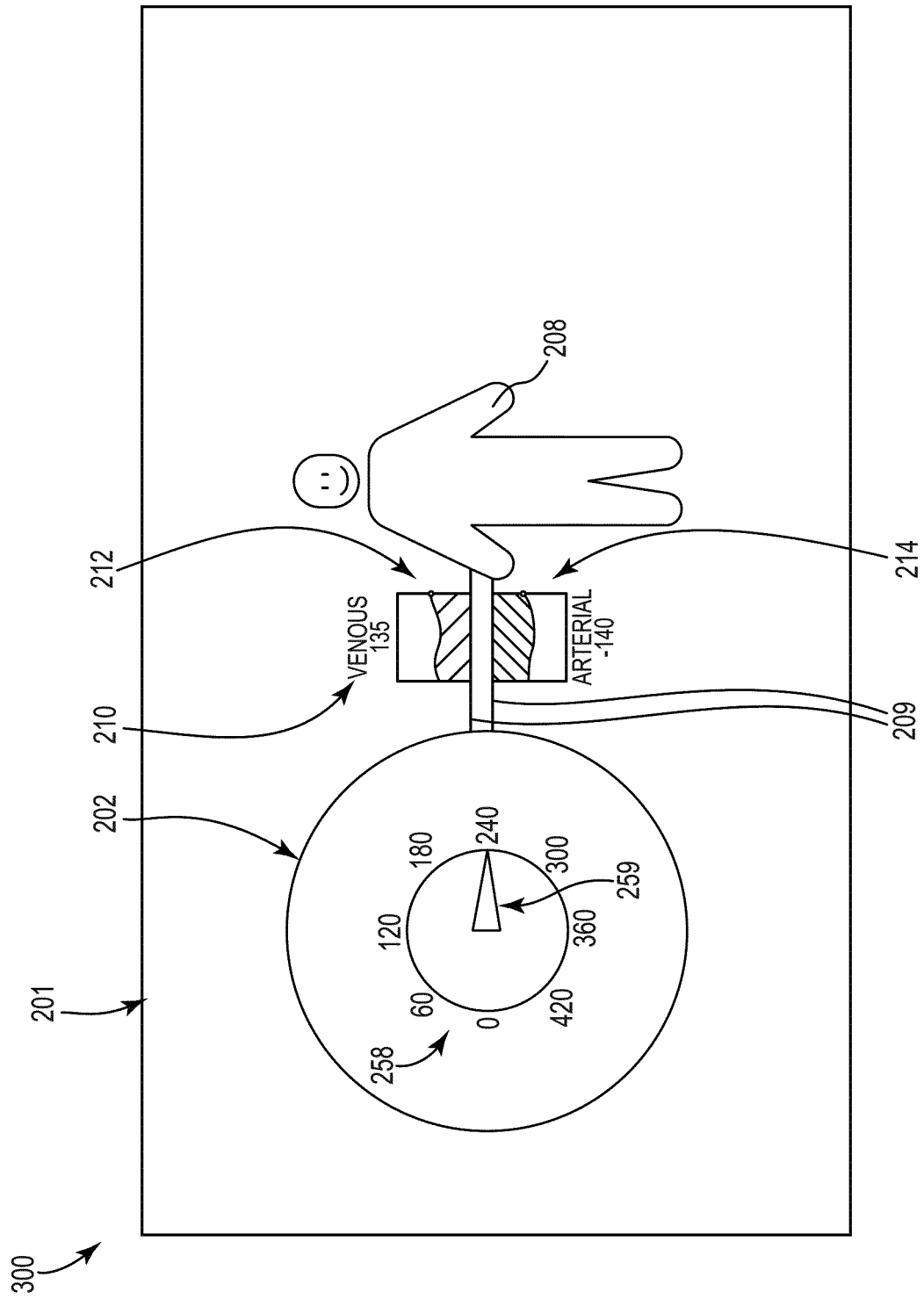

In another embodiment, the blood circuit pressure graphical element 210 may be located, or positioned, between the blood treatment graphical element 202 and the patient graphical element 208 on the graphical user interface 300 as shown in FIGS. 6A-6B to indicate that the venous and arterial blood circuit pressures are monitored from the venous and arterial blood circuits (e.g., in the connections between the blood treatment apparatus of the system performing the one or more blood treatment processes and the patient) Additionally, one or more blood lines 209 may extend from the patient graphical element 208 to the blood treatment graphical element 202 to indicate that the patient is connected to the extracorporeal blood treatment system for the blood treatment. Further, in one or more embodiments, the venous and arterial blood circuit pressures may be monitored by pressure sensors located at the distal ends of the blood lines extending from the patient (e.g., before the apparatus used to perform the blood treatment), and the blood circuit pressure graphical element 210 may be located along the graphical representation of the one or more blood lines 209 to, e.g., be graphically representative of the fact that the venous and arterial blood circuit pressures may be monitored by pressure sensors located at, or coupled to, the distal end portions of the blood lines extending from the patient. Further, as shown, one blood line 209 may be associated and connected with the venous portion 212 of the blood circuit pressure graphical element 210, and as such, may be representative of the venous, or return, blood line, and another blood line 209 may be associated and connected with the arterial portion 214 of the blood circuit pressure graphical element 210, and as such, may be representative of the arterial, or withdrawal, blood line.

Further, the exemplary graphical user interfaces 300 depicted in FIGS. 6A-6B may include a blood flow rate area 258 that is different in appearance from the blood flow rate area 250 of FIGS. 3B-3F. In these embodiments, the blood flow rate area 258 may be described as a circular, "dial"-type graphical element including a blood flow rate adjustment graphical element 259 that indicates the present blood flow rate by "pointing at" the present blood flow rate located around the dial. The blood flow rate adjustment graphical element 259 may be further selected (e.g., touch, swiped, etc.) by a user to change, or adjust, the blood flow rate. The blood flow rate area 258 and the blood flow rate adjustment graphical element 259 may be located anywhere on the exemplary graphical user interfaces. For example, as shown in FIG. 6A, the blood flow rate area 258 and the blood flow rate adjustment graphical element 259 are located in, or proximate to, the upper right corner of the graphical user interface 200. Further, for example, in FIG. 6B, the blood flow rate area 258 and the blood flow rate adjustment graphical element 259 is located within, or as a part of, the blood treatment graphical element 202. More specifically, in this embodiment, the blood flow rate area 258 and the blood flow rate adjustment graphical element 259 may be described as being centrally located inside the circular blood treatment graphical element 202.

Similar to the blood flow adjustment element 254 of FIGS. 3B-3F, when the blood flow rate is adjusted using the blood flow rate adjustment graphical element 259, the blood circuit pressure graphical element 210 may be graphically emphasized in response thereto. For example, the blood circuit pressure graphical element 210 may be highlighted, may blink or flash, may change color, and/or may move to show graphical emphasis in response to, or in view of, the blood flow rate change or adjustment.

The venous portion 212, portions thereof, and associated blood line 209 may be a different color than the arterial portion 214, portions thereof, and associated blood line 209. For example, the venous portion 212, portions thereof, and associated blood line 209 may be blue, and the arterial portion 214, portions thereof, and associated blood line 209 may be red.

The blood circuit pressure graphical element 210 and portions thereof may change in size in response to various events such as alarms or user interactions such as selections. When the size of the blood circuit pressure graphical element 210 and portions thereof is changed, more information with respect to the previously-monitored and presently-monitored blood circuit pressure values may be depicted graphically. For example, more previously-monitored blood circuit pressure values may be displayed graphically or the same amount of previously-monitored blood circuit pressure values may be displayed graphically over a larger portion of the graphical user interface 200. Further, for example, the range of displayable blood circuit pressure values may be increased, e.g., beyond the alarm limits.

Further, the blood circuit pressure graphical element 210 and portions thereof may be graphical emphasized, which may include size changes, in response to various events such as alarms or user interactions such as selections.

Additionally, other portions of the graphical user 200, or the remainder of the graphical user 200 that is not emphasized may be graphically de-emphasized.

Size changes and graphical emphasis of the blood circuit pressure graphical element 210 will be described herein with respect to FIGS. 3D-3F and FIG. 7. As show in FIG. 3D, if a measured blood circuit pressure value approaches an alarm limit, the extracorporeal blood treatment system may issue an alarm or alert. When an alarm is issued, an alarm graphical region 290 may be displayed on the graphical user interface 200. The alarm graphical region 290 is depicted towards the bottom of the graphical user interface 200 and indicates a "High Venous Pressure!" Upon the issuance of an alarm, the system may further deliver various other types of notifications to an operator such as, e.g., sounds, electronic messages, flashing lights, etc.

Further, if the alarm is associated with either blood circuit pressures, at least a portion of the blood circuit pressure graphical element 210 may be graphically emphasized. For example, a portion or all of the blood circuit pressure graphical element 210 may flash, change color, and/or change size. In other words, when the system enters a blood circuit pressure alarm state, the blood circuit pressure graphical element 210 may be graphically emphasized to draw a user's attention to the blood circuit pressure graphical element 210.

In some embodiments, the graphical size of the entire or a portion of the blood circuit pressure graphical element 210 may be increased in response to issuance of the blood circuit pressure alarm state. Further, in some embodiments, a user may select the blood circuit pressure graphical element 210 or portion thereof, and in response to the selection, the graphical size of the entire or a portion of the blood circuit pressure graphical element 210 may be increased.

Figure 3D:
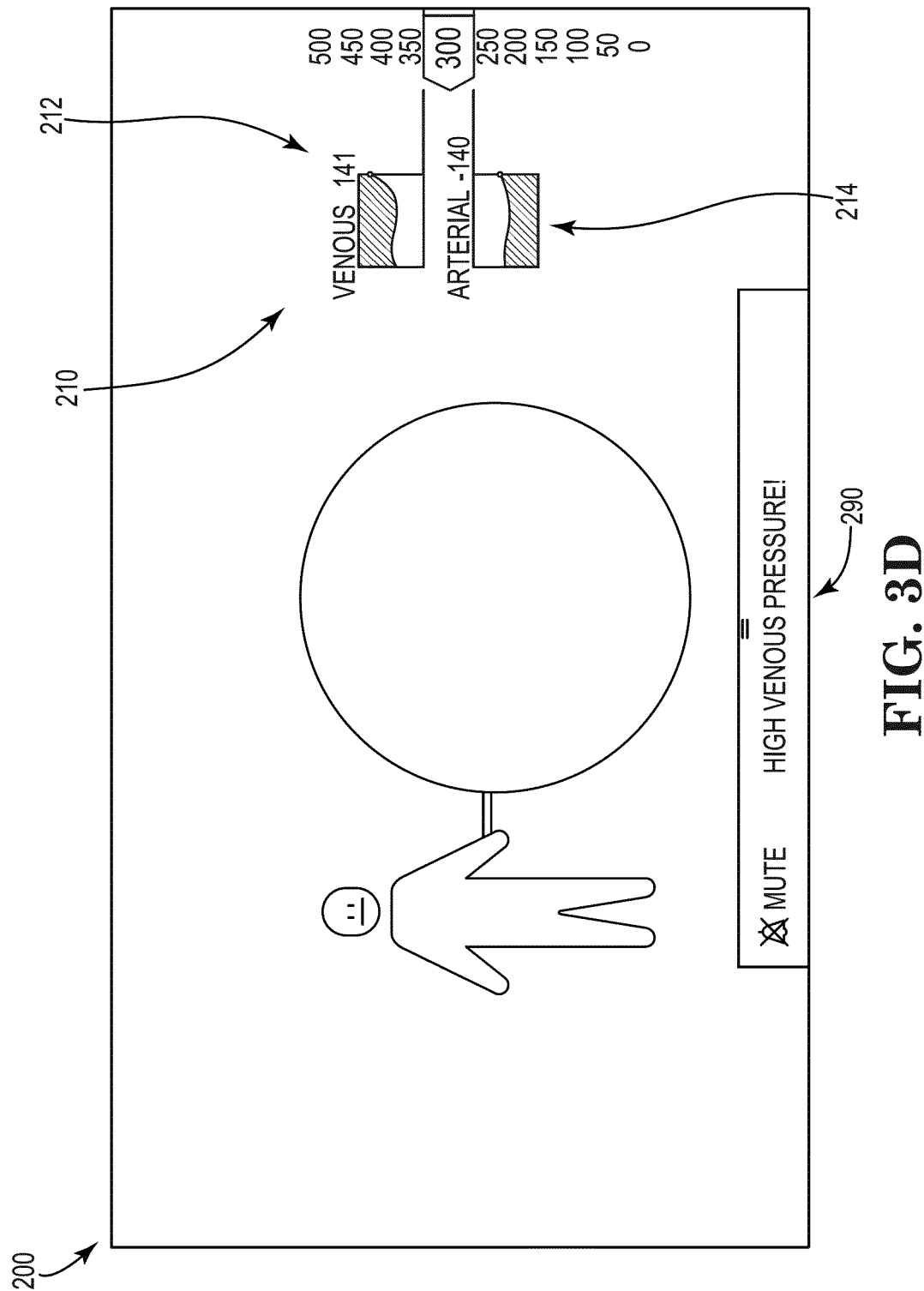

In FIG. 3E, the graphical size of the venous portion 212 of the blood circuit pressure graphical element 210 has been increased, e.g., either automatically in response to an alarm state of FIG. 3D or upon selection by a user. In particular, the graph 217 depicting the graphical representation of the previously-monitored venous blood circuit pressure values 219 has increased in the x and y directions to show more data in each direction. In this embodiment, the length of time, or the trailing time period, has been increased such that more previously-monitored venous blood circuit pressure values 219 may be graphically depicted, and the range of displayable venous blood circuit pressure values has also been increased in both directions beyond the alarm limits. The graph 217 may further include a plurality of time indications, or tick marks, 205 located along the x-axis to indicate the scale of the x-axis. As described herein, the trailing time period 224 of the graph 217 may be a non-linear time period, and as such, the time indications 205 proximate the right side of the graph 217 are spaced further apart from one another than the time indications 205 proximate the left side of the graph 217. In other words, longer periods of time extend between time indications 205 on the right side of the graph 217 while shorter periods of time extend between time indications 205 on the left side of the graph 217.

Additionally, as shown in FIG. 3E, the other portions, regions, areas, and elements other than the enlarged, or expanded, venous portion 212 of the blood circuit pressure graphical element 210, or the remainder of the graphical user interface 200, may be graphically de-emphasized in response to the issuance of the blood circuit pressure alarm state. As such, the de-emphasis may further direct a user's attention to the emphasized portion, namely, the enlarged, or expanded, venous portion 212 of the blood circuit pressure graphical element 210. The de-emphasization may include graying-out, de-colorizing, tinting, low-lighting, etc. the remainder of the graphical user interface 200.

In one or more embodiments, the graphical size of the venous portion 212 of the blood circuit pressure graphical element 210 and/or the graphical size of the arterial portion 214 of the blood circuit pressure graphical element 210 may be increased in response to, or triggered by, a blood flow rate adjustment, e.g., which may be adjusted by a user using the blood flow rate adjustment graphical element 254. Further, the graphical size of the venous portion 212 and/or the arterial portion 214 of the blood circuit pressure graphical element 210 may be increased for a selected time period (e.g., 5 seconds) such that, e.g., a user may be able to see a more detailed view of the venous and arterial blood circuit pressure information displayed by the blood circuit pressure graphical element 210 during blood flow rate adjustment and/or for a period thereafter. After the selected time period expires, the graphical size of the venous portion 212 and/or arterial portion 214 of the blood circuit pressure graphical element 210 may be decreased. In other words, one or more portions or regions of the blood circuit pressure graphical element 210 may be temporarily increased in graphical size in response to, or triggered by, a blood flow rate adjustment.

A user may graphically de-emphasize the venous portion 212 of the blood circuit pressure graphical element 210 shown in FIG. 3E back to as shown in FIG. 3D by, e.g., selecting a portion of the graphical user interface 200 other than the blood circuit pressure graphical element 210. Additionally, the venous portion 212 of the blood circuit pressure graphical element 210 may be de-emphasized if, e.g., the venous blood circuit pressure changes to an acceptable value (e.g., within the range of alarm limits).

Figure 3F:
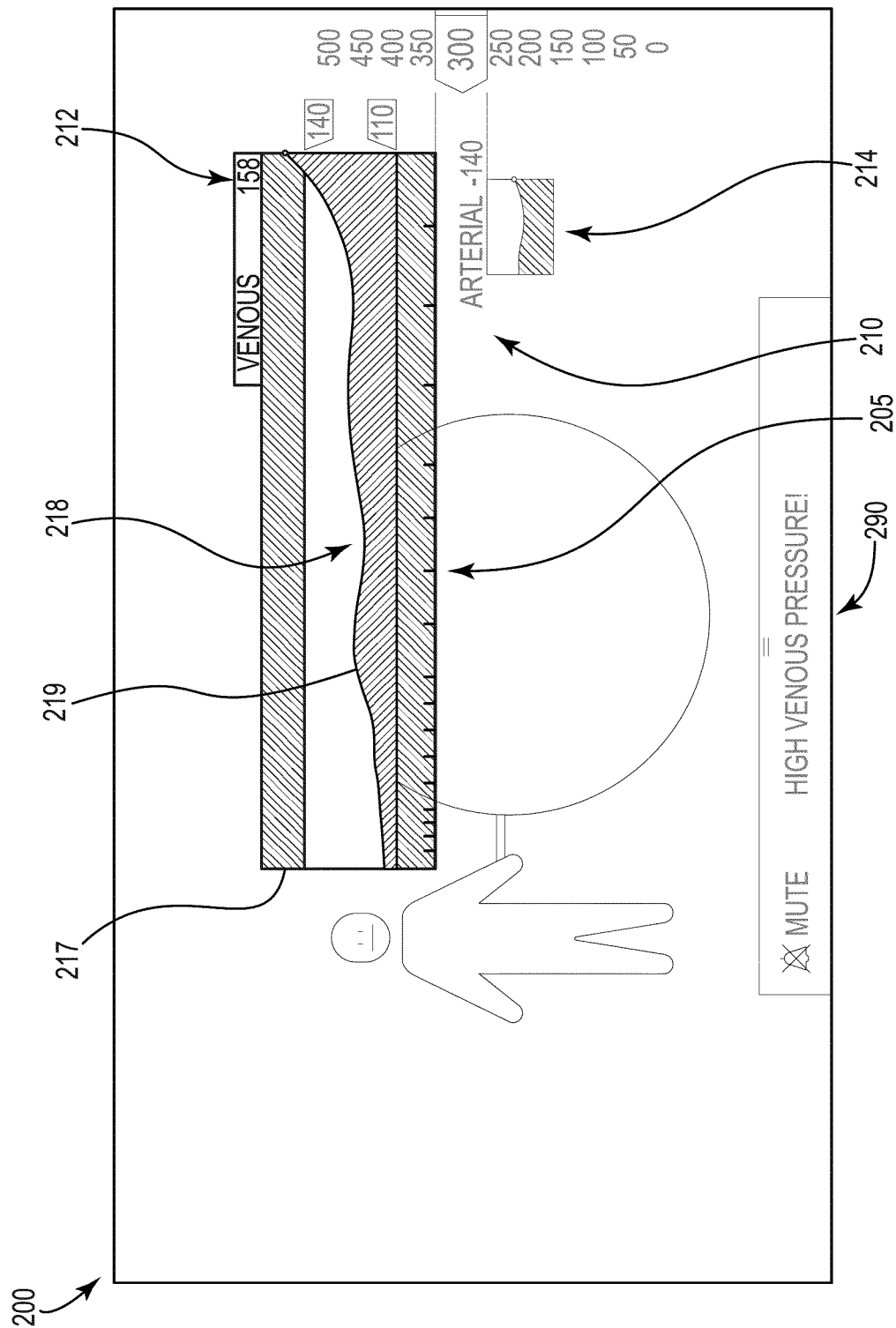

The graphical size of the venous portion 212 of the blood circuit pressure graphical element 210 may be further increased as shown in FIG. 3F. In particular, the x-axis of the graph 217 of the graphical representation of the previously-monitored venous blood circuit pressure values 218 has been increased in FIG. 3F. In this embodiment, although the x-axis of the graph 217 of the graphical representation of the previously-monitored venous blood circuit pressure values 218 has been increased, the time period, or trailing time period, depicted over the x-axis has remained the same as shown in FIG. 3E. The expansion of the x-axis, however, may depict the graphical representation of the previously-monitored venous blood circuit pressure values 218 in more detail (e.g., the line graph may have more room to depict more detail of the previously-monitored venous blood circuit pressure values 219 along the x-axis of the graph 217).

Figure 7:
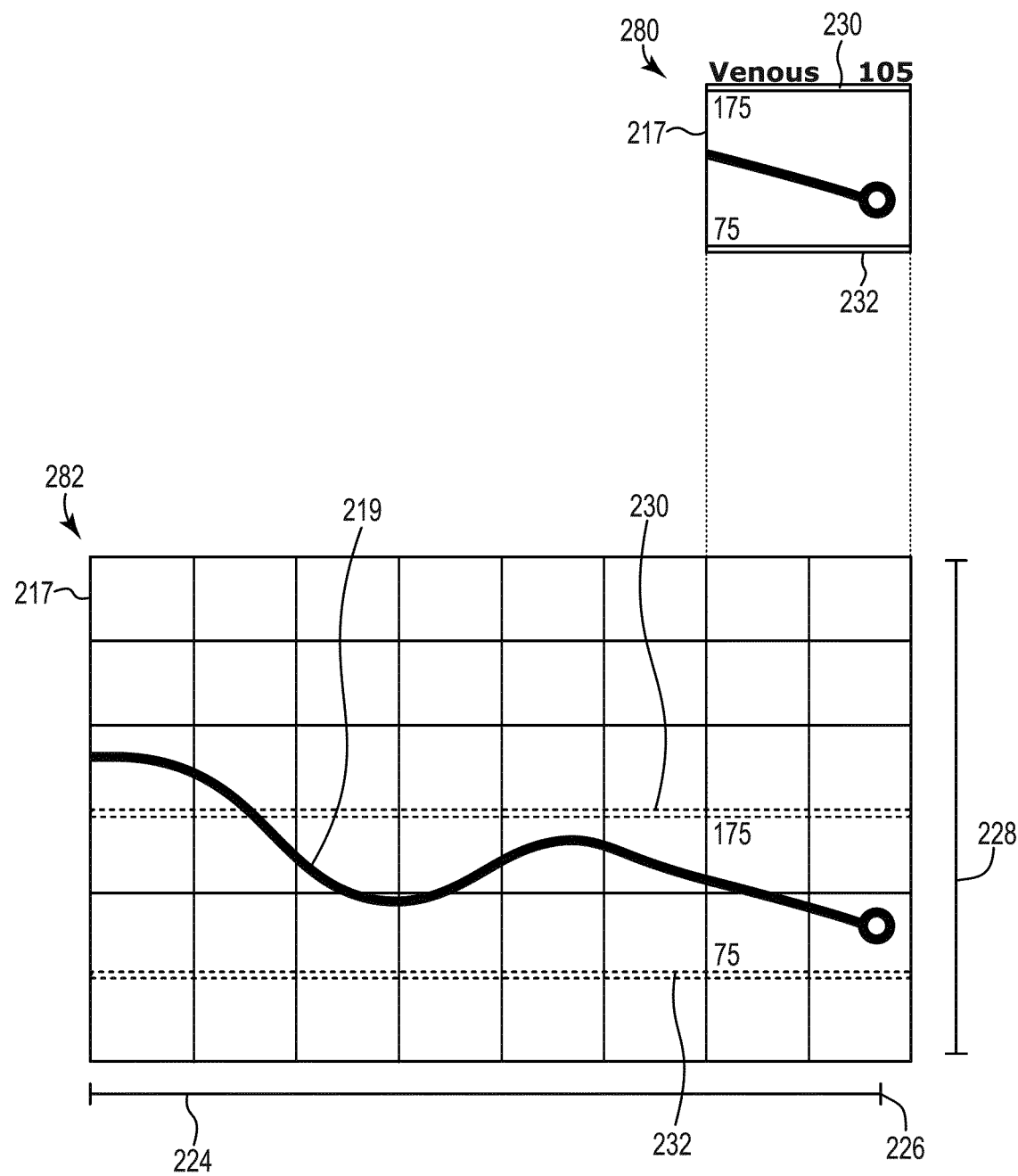
FIG. 7 depicts an un-expanded venous portion and an expanded venous portion of an exemplary blood circuit pressure graphical element of the graphical user interface of FIGS. 3B-3F.

Another example of the venous portion 212 increasing in graphical size is depicted in FIG. 7. As shown, an unexpanded venous portion 280 may be expanded, or increased in graphical size to, the expanded venous portion 282. As shown, the range 228 of displayable venous blood circuit pressure values has been increased beyond the venous blood circuit pressure alarm limit graphical representations 230, 232 and the trailing time period 224 has expanded to show more previously-monitored venous blood circuit pressure values (e.g., a longer graphical representation, or line representing, previously-monitored venous blood circuit pressure values 219).

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. An extracorporeal blood treatment system comprising:
an extracorporeal blood treatment apparatus to perform an extracorporeal blood treatment, the extracorporeal blood treatment apparatus comprising:
one or more pumps,
a venous blood circuit,
an arterial blood circuit, and
two or more blood circuit pressure sensors to measure venous blood circuit pressure in the venous blood circuit and arterial blood circuit pressure in the arterial blood circuit;
a display comprising a graphical user interface configured to depict a blood circuit pressure graphical element corresponding to the measured venous blood circuit pressure and arterial blood circuit pressure and a blood flow rate area corresponding to blood flow rate of the extracorporeal blood treatment performable using the extracorporeal blood treatment apparatus; and
a processor operatively coupled to the display and the extracorporeal blood treatment apparatus, wherein the processor is configured to:
monitor blood flow rate of the extracorporeal blood treatment;
display the blood flow rate area on the graphical user interface depicting a present blood flow rate value of the extracorporeal blood treatment and comprising a blood flow rate adjustment graphical element,
allow a user to move the blood flow rate adjustment graphical element to adjust the blood flow rate of the extracorporeal blood treatment using the one or more pumps of the extracorporeal blood treatment apparatus,
monitor venous blood circuit pressure in the venous blood circuit and arterial blood circuit pressure in the arterial blood circuit of the extracorporeal blood treatment using the two or more blood circuit pressure sensors of the extracorporeal blood treatment apparatus, and
display the blood circuit pressure graphical element on the graphical user interface, wherein the blood circuit pressure graphical element is graphically emphasized in response to the blood flow rate adjustment graphical element being moved to adjust the blood flow rate of the extracorporeal blood treatment using the one or more pumps of the extracorporeal blood treatment apparatus, wherein the blood circuit pressure graphical element comprises:
a venous portion comprising:
a presently-monitored venous blood circuit pressure value of the extracorporeal blood treatment, and
a graphical representation of previously-monitored venous blood circuit pressure values of the extracorporeal blood treatment, and
an arterial portion comprising:
a presently-monitored arterial blood circuit pressure value of the extracorporeal blood treatment, and
a graphical representation of previously-monitored arterial blood circuit pressure values of the extracorporeal blood treatment.

2. A method for an extracorporeal blood treatment system comprising:
providing an extracorporeal blood treatment apparatus to perform an extracorporeal blood treatment, the extracorporeal blood treatment apparatus comprising:
one or more pumps,
a venous blood circuit,
an arterial blood circuit, and
two or more blood circuit pressure sensors to measure venous blood circuit pressure in the venous blood circuit and arterial blood circuit pressure in the arterial blood circuit;
monitoring blood flow rate of the extracorporeal blood treatment;
displaying a blood flow rate area on a graphical user interface depicting a present blood flow rate value of the extracorporeal blood treatment and comprising a blood flow rate adjustment graphical element;
allowing a user to move the blood flow rate adjustment graphical element to adjust the blood flow rate of the extracorporeal blood treatment using the one or more pumps of the extracorporeal blood treatment apparatus;
monitoring venous blood circuit pressure in the venous blood circuit of the extracorporeal blood treatment using the two or more blood circuit pressure sensors of the extracorporeal blood treatment apparatus and an arterial blood circuit pressure in the arterial blood circuit of the extracorporeal blood treatment using the two or more blood circuit pressure sensors of the extracorporeal blood treatment apparatus; and
displaying a blood circuit pressure graphical element on the graphical user interface, wherein the blood circuit pressure graphical element is graphically emphasized in response to the blood flow rate of the extracorporeal blood treatment being adjusted using the blood flow rate adjustment graphical element, wherein the blood circuit pressure graphical element comprises:
a venous portion comprising:
a presently-monitored venous blood circuit pressure value of the extracorporeal blood treatment, and
a graphical representation of previously-monitored venous blood circuit pressure values of the extracorporeal blood treatment, and
an arterial portion comprising:
a presently-monitored arterial blood circuit pressure value of the extracorporeal blood treatment, and
a graphical representation of previously-monitored arterial blood circuit pressure values of the extracorporeal blood treatment.

3. The system of claim 1, wherein the blood circuit pressure graphical element is displayed in proximity to the blood flow rate adjustment graphical element and moves with the blood flow rate adjustment graphical element in response to the blood flow rate being adjusted using the blood flow rate adjustment graphical element.

4. The system of claim 1, wherein a graphical size of at least a portion of the blood circuit pressure graphical element is expanded in response to the blood flow rate being adjusted using the blood flow rate adjustment graphical element.

5. The system of claim 1, wherein the presently-monitored venous blood circuit pressure value comprises at least one of an alphanumeric representation of the presently-monitored venous blood circuit pressure value and a graphical representation of the presently-monitored venous blood circuit pressure value proximate the graphical representation of previously-monitored venous blood circuit pressure values, and wherein the presently-monitored arterial blood circuit pressure value comprises at least one of an alphanumeric representation of the presently-monitored arterial blood circuit pressure value and a graphical representation of the presently-monitored arterial blood circuit pressure value proximate the graphical representation of previously-monitored arterial blood circuit pressure values.

6. The system of claim 1, wherein the venous portion of the blood circuit pressure graphical element further comprises a venous circuit pressure alarm limit graphical representation indicative of a venous circuit pressure alarm limit value for the monitored venous blood circuit pressure, wherein the venous circuit pressure alarm limit graphical representation is located in relation to the presently-monitored venous blood circuit pressure value to graphically indicate a quantitative difference between the presently-monitored venous blood circuit pressure value and the venous circuit pressure alarm limit value,
wherein the arterial portion of the blood circuit pressure graphical element further comprises an arterial circuit pressure alarm limit graphical representation indicative of a arterial circuit pressure alarm limit value for the monitored arterial blood circuit pressure, wherein the arterial circuit pressure alarm limit graphical representation is located in relation to the presently-monitored arterial blood circuit pressure value to graphically indicate a quantitative difference between the presently-monitored arterial blood circuit pressure value and the arterial circuit pressure alarm limit value,
wherein the processor is further configured to:
allow a user to select the venous circuit pressure alarm limit graphical representation to adjust the venous circuit pressure alarm limit value, and
allow a user to select the arterial circuit pressure alarm limit graphical representation to adjust the arterial circuit pressure alarm limit value.

7. The system of claim 6, wherein the processor is further configured to:
allow a user to select and drag the venous circuit pressure alarm limit graphical representation upwardly to increase the venous circuit pressure alarm limit value and downwardly to decrease the venous circuit pressure alarm limit value, and
allow a user to select and drag the arterial circuit pressure alarm limit graphical representation upwardly to increase the arterial circuit pressure alarm limit value and downwardly to decrease the arterial circuit pressure alarm limit value.

8. The system of claim 6, wherein the venous circuit pressure alarm limit graphical representation is only displayed in response to the presently-monitored venous blood circuit pressure value being within a selected value of the venous circuit pressure alarm limit value, and wherein the arterial circuit pressure alarm limit graphical representation is only displayed in response to the presently-monitored arterial blood circuit pressure value being within a selected value of the arterial circuit pressure alarm limit value.

9. The system of claim 1, wherein the venous portion of the blood circuit pressure graphical element further comprises:
an upper venous circuit pressure alarm limit graphical representation indicative of an upper venous circuit pressure alarm limit value for the monitored venous blood circuit pressure, and
a lower venous circuit pressure alarm limit graphical representation indicative of a lower venous circuit pressure alarm limit value for the monitored venous blood circuit pressure, wherein the upper and lower venous circuit pressure alarm limit graphical representations are located in relation to the presently-monitored venous blood circuit pressure value to graphically indicate quantitative differences between the presently-monitored venous blood circuit pressure value and the upper and lower venous circuit pressure alarm limit values,
wherein the processor is further configured to allow a user to select and drag the venous portion upwardly to simultaneously increase both of the upper and lower venous circuit pressure alarm limit values and downwardly to simultaneously decrease both of the upper and lower venous circuit pressure alarm limit values,
wherein the arterial portion of the blood circuit pressure graphical element further comprises:
an upper arterial circuit pressure alarm limit graphical representation indicative of an upper arterial circuit pressure alarm limit value for the monitored arterial blood circuit pressure, and
a lower arterial circuit pressure alarm limit graphical representation indicative of a lower arterial circuit pressure alarm limit value for the monitored arterial blood circuit pressure, wherein the upper and lower arterial circuit pressure alarm limit graphical representations are located in relation to the presently-monitored arterial blood circuit pressure value to graphically indicate quantitative differences between the presently-monitored arterial blood circuit pressure value and the upper and lower arterial circuit pressure alarm limit values,
wherein the processor is further configured to allow a user to select and drag the arterial portion upwardly to simultaneously increase both of the upper and lower arterial circuit pressure alarm limit values and downwardly to simultaneously decrease both of the upper and lower arterial circuit pressure alarm limit values.

10. The system of claim 9, wherein the processor is further configured to allow a user to automatically reset both of the upper and lower venous circuit pressure alarm limit values centered around the presently-monitored venous blood circuit pressure value and allowing a user to automatically reset both of the upper and lower arterial circuit pressure alarm limit values centered around the presently-monitored arterial blood circuit pressure value.

11. The system of claim 1, wherein the graphical representation of previously-monitored venous blood circuit pressure values comprises a venous blood circuit pressure line graph plotting the previously-monitored venous blood circuit pressure values over a trailing time period prior to the present, and wherein the graphical representation of previously-monitored arterial blood circuit pressure values comprises an arterial blood circuit pressure line graph plotting the previously-monitored arterial blood circuit pressure values over the trailing time period prior to the present.

12. The system of claim 11, wherein the trailing time period is a non-linear time period.

13. The system of claim 11, wherein the venous portion of the blood circuit pressure graphical element is selectable by a user to expand a graphical size of the venous portion on the graphical user interface increasing the displayable trailing time period of the venous blood circuit pressure line graph, and wherein the arterial portion of the blood circuit pressure graphical element is selectable by a user to expand a graphical size of the arterial portion on the graphical user interface increasing the displayable trailing time period of the arterial blood circuit pressure line graph.

14. The system of claim 13, wherein expanding the graphical size of the venous portion further increases the displayable range of venous blood circuit pressure values of the venous blood circuit pressure line graph, and wherein expanding the graphical size of the arterial portion further increases the displayable range of arterial blood circuit pressure values of the arterial blood circuit pressure line graph.

15. The system of claim 1, wherein the blood circuit pressure graphical element is only displayed on the graphical user interface in response to the patient being connected to at least one of the venous and arterial blood circuits of the extracorporeal blood treatment system.

16. The system of claim 1, wherein at least one of the venous portion and the arterial portion of the blood circuit pressure graphical element is graphically emphasized in response to issuance of a blood circuit pressure alarm state.

17. The system of claim 16, wherein a graphical size of at least one of the venous portion and the arterial portion of the blood circuit pressure graphical element on the graphical user interface is increased in response to issuance of the blood circuit pressure alarm state.

18. The system of claim 16, wherein the graphical user interface other than the at least one of the venous portion and the arterial portion of the blood circuit pressure graphical element that is graphically emphasized is graphically de-emphasized in response to issuance of the blood circuit pressure alarm state.

19. The system of claim 1, wherein the display comprises a touchscreen.

20. An extracorporeal blood treatment system comprising:
an extracorporeal blood treatment apparatus to perform an extracorporeal blood treatment, the extracorporeal blood treatment apparatus comprising:
one or more pumps,
a venous blood circuit,
an arterial blood circuit,
one or more blood flow rate sensors, and
two or more blood circuit pressure sensors to measure venous blood circuit pressure in the venous blood circuit and the arterial blood circuit pressure in an arterial blood circuit;
a display comprising a graphical user interface configured to depict a blood circuit pressure graphical element corresponding to the measured venous blood circuit pressure and arterial blood circuit pressure, a blood treatment graphical element corresponding to one or more blood treatment processes of the extracorporeal blood treatment performable using the extracorporeal blood treatment apparatus, a blood flow rate adjustment graphical element, and a patient graphical element symbolically depicting a patient undergoing the extracorporeal blood treatment using the extracorporeal blood treatment apparatus; and
a processor operatively coupled to the display and the extracorporeal blood treatment apparatus, wherein the processor is configured to:
monitor venous blood circuit pressure in the venous blood circuit and arterial blood circuit pressure in the arterial blood circuit using the two or more blood circuit pressure sensors of the extracorporeal blood treatment apparatus,
monitor blood flow rate of the extracorporeal blood treatment using the one or more blood flow rate sensors;
display the blood treatment graphical element and the patient graphical element on the graphical user interface, and
display the blood circuit pressure graphical element between the blood treatment graphical element and the patient graphical element on the graphical user interface to indicate that the venous and arterial blood circuit pressures are monitored from the venous and arterial blood circuits of the extracorporeal blood treatment apparatus,
wherein the blood circuit pressure graphical element comprises:
a venous portion comprising:
a presently-monitored venous blood circuit pressure value of the extracorporeal blood treatment, and
a graphical representation of previously-monitored venous blood circuit pressure values of the extracorporeal blood treatment, and
an arterial portion comprising:
a presently-monitored arterial blood circuit pressure value of the extracorporeal blood treatment, and
a graphical representation of previously-monitored arterial blood circuit pressure values of the extracorporeal blood treatment.

21. The system of claim 20, wherein the blood circuit pressure graphical element is displayed in proximity to the blood flow rate adjustment graphical element and moves with the blood flow rate adjustment graphical element in response to the blood flow rate being adjusted using the blood flow rate adjustment graphical element.

22. The system of claim 20, wherein a graphical size of at least a portion of the blood circuit pressure graphical element is expanded in response to the blood flow rate being adjusted using the blood flow rate adjustment graphical element.

23. The system of claim 20, wherein the presently-monitored venous blood circuit pressure value comprises at least one of an alphanumeric representation of the presently-monitored venous blood circuit pressure value and a graphical representation of the presently-monitored venous blood circuit pressure value proximate the graphical representation of previously-monitored venous blood circuit pressure values, and wherein the presently-monitored arterial blood circuit pressure value comprises at least one of an alphanumeric representation of the presently-monitored arterial blood circuit pressure value and a graphical representation of the presently-monitored arterial blood circuit pressure value proximate the graphical representation of previously-monitored arterial blood circuit pressure values.

24. The system of claim 20, wherein the venous portion of the blood circuit pressure graphical element further comprises a venous circuit pressure alarm limit graphical representation indicative of a venous circuit pressure alarm limit value for the monitored venous blood circuit pressure, wherein the venous circuit pressure alarm limit graphical representation is located in relation to the presently-monitored venous blood circuit pressure value to graphically indicate a quantitative difference between the presently-monitored venous blood circuit pressure value and the venous circuit pressure alarm limit value,
wherein the arterial portion of the blood circuit pressure graphical element further comprises an arterial circuit pressure alarm limit graphical representation indicative of a arterial circuit pressure alarm limit value for the monitored arterial blood circuit pressure, wherein the arterial circuit pressure alarm limit graphical representation is located in relation to the presently-monitored arterial blood circuit pressure value to graphically indicate a quantitative difference between the presently-monitored arterial blood circuit pressure value and the arterial circuit pressure alarm limit value,
wherein the processor is further configured to:

allow a user to select the venous circuit pressure alarm limit graphical representation to adjust the venous circuit pressure alarm limit value, and allow a user to select the arterial circuit pressure alarm limit graphical representation to adjust the arterial circuit pressure alarm limit value.

25. The system of claim 24, wherein the processor is further configured to:

allow a user to select and drag the venous circuit pressure alarm limit graphical representation upwardly to increase the venous circuit pressure alarm limit value and downwardly to decrease the venous circuit pressure alarm limit value, and allow a user to select and drag the arterial circuit pressure alarm limit graphical representation upwardly to increase the arterial circuit pressure alarm limit value and downwardly to decrease the arterial circuit pressure alarm limit value.

26. The system of claim 24, wherein the venous circuit pressure alarm limit graphical representation is only displayed in response to the presently-monitored venous blood circuit pressure value being within a selected value of the venous circuit pressure alarm limit value, and wherein the arterial circuit pressure alarm limit graphical representation is only displayed in response to the presently-monitored arterial blood circuit pressure value being within a selected value of the arterial circuit pressure alarm limit value.

27. The system of claim 20, wherein the venous portion of the blood circuit pressure graphical element further comprises:

an upper venous circuit pressure alarm limit graphical representation indicative of an upper venous circuit pressure alarm limit value for the monitored venous blood circuit pressure, and a lower venous circuit pressure alarm limit graphical representation indicative of a lower venous circuit pressure alarm limit value for the monitored venous blood circuit pressure, wherein the upper and lower venous circuit pressure alarm limit graphical representations are located in relation to the presently-monitored venous blood circuit pressure value to graphically indicate quantitative differences between the presently-monitored venous blood circuit pressure value and the upper and lower venous circuit pressure alarm limit values, wherein the processor is further configured to allow a user to select and drag the venous portion upwardly to simultaneously increase both of the upper and lower venous circuit pressure alarm limit values and downwardly to simultaneously decrease both of the upper and lower venous circuit pressure alarm limit values, wherein the arterial portion of the blood circuit pressure graphical element further comprises:

an upper arterial circuit pressure alarm limit graphical representation indicative of an upper arterial circuit pressure alarm limit value for the monitored arterial blood circuit pressure, and a lower arterial circuit pressure alarm limit graphical representation indicative of a lower arterial circuit pressure alarm limit value for the monitored arterial blood circuit pressure, wherein the upper and lower arterial circuit pressure alarm limit graphical representations are located in relation to the presently-monitored arterial blood circuit pressure value to graphically indicate quantitative differences between the presently-monitored arterial blood circuit pressure value and the upper and lower arterial circuit pressure alarm limit values, wherein the processor is further configured to allow a user to select and drag the arterial portion upwardly to simultaneously increase both of the upper and lower arterial circuit pressure alarm limit values and downwardly to simultaneously decrease both of the upper and lower arterial circuit pressure alarm limit values.

28. The system of claim 27, wherein the processor is further configured to allow a user to automatically reset both of the upper and lower venous circuit pressure alarm limit values centered around the presently-monitored venous blood circuit pressure value and allowing a user to automatically reset both of the upper and lower arterial circuit pressure alarm limit values centered around the presently-monitored arterial blood circuit pressure value.

29. The system of claim 20, wherein the graphical representation of previously-monitored venous blood circuit pressure values comprises a venous blood circuit pressure line graph plotting the previously-monitored venous blood circuit pressure values over a trailing time period prior to the present, and wherein the graphical representation of previously-monitored arterial blood circuit pressure values comprises an arterial blood circuit pressure line graph plotting the previously-monitored arterial blood circuit pressure values over the trailing time period prior to the present.

30. The system of claim 29, wherein the trailing time period is a non-linear time period.

31. The system of claim 29, wherein the venous portion of the blood circuit pressure graphical element is selectable by a user to expand a graphical size of the venous portion on the graphical user interface increasing the displayable trailing time period of the venous blood circuit pressure line graph, and wherein the arterial portion of the blood circuit pressure graphical element is selectable by a user to expand a graphical size of the arterial portion on the graphical user interface increasing the displayable trailing time period of the arterial blood circuit pressure line graph.

32. The system of claim 31, wherein expanding the graphical size of the venous portion further increases the displayable range of venous blood circuit pressure values of the venous blood circuit pressure line graph, and wherein expanding the graphical size of the arterial portion further increases the displayable range of arterial blood circuit pressure values of the arterial blood circuit pressure line graph.

33. The system of claim 20, wherein the graphical user interface is configured to depict a graphical representation of one or more blood lines extending from the patient graphical element to the blood treatment graphical element to indicate that the patient is connected to the extracorporeal blood treatment system for the extracorporeal blood treatment, wherein the blood circuit pressure graphical element is located along the graphical representation of the one or more blood lines.

34. The system of claim 20, wherein the blood circuit pressure graphical element is only displayed on the graphical user interface in response to the patient being connected to at least one of the venous and arterial blood circuits of the extracorporeal blood treatment system.

35. The system of claim 20, wherein at least one of the venous portion and the arterial portion of the blood circuit pressure graphical element is graphically emphasized in response to issuance of a blood circuit pressure alarm state.

36. The system of claim 35, wherein a graphical size of at least one of the venous portion and the arterial portion of the blood circuit pressure graphical element on the graphical user interface is increased in response to issuance of the blood circuit pressure alarm state.

37. The system of claim 35, wherein the graphical user interface other than the at least one of the venous portion and the arterial portion of the blood circuit pressure graphical element that is graphically emphasized is graphically de-emphasized in response to issuance of the blood circuit pressure alarm state.

38. The system of claim 20, wherein the display comprises a touchscreen.

* * * * *